US008946301B2

(12) United States Patent
Perrin et al.

(10) Patent No.: US 8,946,301 B2
(45) Date of Patent: Feb. 3, 2015

(54) TARGETING OF T-LYMPHOCYTES TO TREAT AMYOTROPHIC LATERAL SCLEROSIS

(71) Applicant: ALS Therapy Development Institute, Cambridge, MA (US)

(72) Inventors: Steven Perrin, Newbury, MA (US); John Lincecum, Jamaica Plain, MA (US); Alan Gill, Reading, MA (US); Fernando Vieira, Newton, MA (US)

(73) Assignee: ALS Therapy Development Institute, Cambridge, MA (US)

( * ) Notice: Subject to any disclaimer, the term of this patent is extended or adjusted under 35 U.S.C. 154(b) by 0 days.

(21) Appl. No.: 13/689,375

(22) Filed: Nov. 29, 2012

(65) Prior Publication Data

US 2013/0150454 A1 Jun. 13, 2013

Related U.S. Application Data

(60) Provisional application No. 61/564,515, filed on Nov. 29, 2011.

(51) Int. Cl.
| | | |
|---|---|---|
| *A01N 33/02* | (2006.01) | |
| *A61K 31/135* | (2006.01) | |
| *C07C 215/20* | (2006.01) | |
| *A61K 31/145* | (2006.01) | |
| *A61K 31/137* | (2006.01) | |

(52) U.S. Cl.
CPC ............ *C07C 215/20* (2013.01); *A61K 31/145* (2013.01); *A61K 31/137* (2013.01)
USPC ........................................................ 514/653

(58) Field of Classification Search
None
See application file for complete search history.

(56) References Cited

U.S. PATENT DOCUMENTS

| | | |
|---|---|---|
| 5,135,956 A | 8/1992 | Borg |
| 5,395,822 A | 3/1995 | Izumi |
| 5,604,229 A | 2/1997 | Fujita |
| 5,906,976 A | 5/1999 | Vardimon |
| 6,008,192 A | 12/1999 | Al-Razzak |
| 6,333,051 B1 | 12/2001 | Kabanov |
| 6,387,406 B1 | 5/2002 | Kabanov |
| 7,456,157 B2 | 11/2008 | Kohno |
| 2004/0057902 A1 | 3/2004 | Gold |
| 2005/0090520 A1 | 4/2005 | Lindquist |
| 2009/0176744 A1 | 7/2009 | Liu |

FOREIGN PATENT DOCUMENTS

| | | |
|---|---|---|
| EP | 0627406 | 12/1994 |
| WO | 2005025553 | 3/2005 |
| WO | WO 2008135522 A1 * | 11/2008 |

OTHER PUBLICATIONS

What is ALS?, The ALS Associate, 2010, http://www.alsa.org/about-als/what-is-als.html.*
[No Author Listed] Gilenya (fingolimod). FDA Label. Approved in 2010. 22 pages.
Anselmo et al., FTY720 pretreatment reduces warm hepatic ischemia reperfusion injury through inhibition of T-lymphocyte infiltration. Am J Transplant. Oct. 2002;2(9):843-9.
Awad et al., Selective sphingosine 1-phosphate 1 receptor activation reduces ischemia-reperfusion injury in mouse kidney. Am J Physiol Renal Physiol. Jun. 2006;290(6):F1516-24. Epub Jan. 10, 2006.
Bolli et al., 2-imino-thiazolidin-4-one derivatives as potent, orally active S1P1 receptor agonists. J Med Chem. May 27, 2010;53(10):4198-211.
Chiu et al., T lymphocytes potentiate endogenous neuroprotective inflammation in a mouse model of ALS. Proc Natl Acad Sci U S A. Nov. 18, 2008;105(46):17913-8. Epub Nov. 7, 2008.
Crosignani et al., Discovery of a novel series of potent S1P1 agonists. Bioorg Med Chem Lett. Mar. 1, 2010;20(5):1516-9. Epub Jan. 25, 2010.
Dal Canto et al., A low expressor line of transgenic mice carrying a mutant human Cu,Zn superoxide dismutase (SOD1) gene develops pathological changes that most closely resemble those in human amyotrophic lateral sclerosis. Acta Neuropathol. Jun. 1997;93(6):537-50.
Foster et al., Brain penetration of the oral immunomodulatory drug FTY720 and its phosphorylation in the central nervous system during experimental autoimmune encephalomyelitis: consequences for mode of action in multiple sclerosis. J Pharmacol Exp Ther. Nov. 2007;323(2):469-75. Epub Aug. 6, 2007.
Gurney et al., Motor neuron degeneration in mice that express a human Cu,Zn superoxide dismutase mutation. Science. Jun. 17, 1994;264(5166):1772-5.
Miron et al., FTY720 modulates human oligodendrocyte progenitor process extension and survival. Ann Neurol. Jan. 2008;63(1):61-71.
Scott et al., Design, power, and interpretation of studies in the standard murine model of ALS. Amyotroph Lateral Scler. 2008;9(1):4-15.
Sensken et al., Accumulation of fingolimod (FTY720) in lymphoid tissues contributes to prolonged efficacy. J Pharmacol Exp Ther. Mar. 2009;328(3):963-9. Epub Dec. 12, 2008.
Takabe et al., "Inside-out" signaling of sphingosine-1-phosphate: therapeutic targets. Pharmacol Rev. Jun. 2008;60(2):181-95. Epub Jun. 13, 2008.
Zhang et al., FTY720 ameliorates experimental autoimmune neuritis by inhibition of lymphocyte and monocyte infiltration into peripheral nerves. Exp Neurol. Apr. 2008;210(2):681-90. Epub Jan. 17, 2008.
Zhang et al., Distribution of Foxp3(+) T-regulatory cells in experimental autoimmune neuritis rats. Exp Neurol. Mar. 2009;216(1):75-82. Epub Dec. 3, 2008.
International Search Report for PCT/US2012/067093 dated Mar. 13, 2013.
Chiba, K., et al. FTY720, a novel immunosuppressant, induces sequestration of circulating mature lymphocytes by acceleration of lymphocyte homing in rats. J of Immunol., 1998, vol. 160, pp. 5037-5044.
Beers et al., PNAS, 2008, vol. 105, pp. 15558-15563.
Duarte et al., J Neurol Sci, 1991, vol. 104, pp. 88-91, abstract.
Friese et al., Brain, 2005, vol. 128, pp. 1747-1763.
Gilenya, Novartis, May 2012.

(Continued)

*Primary Examiner* — Anna Pagonakis
*Assistant Examiner* — Daniel M Podgorski
(74) *Attorney, Agent, or Firm* — Thomas Engellenner; Reza Mollaaghababa; Pepper Hamilton LLP

(57) ABSTRACT

Methods and therapeutic compositions are disclosed for treating neurodegenerative disorders and, in particular Amyotrophic Lateral Sclerosis, using sphingosine1-phosphate receptor modulators, such as fingolimod or a pharmaceutically acceptable salt, hydrate, or solvate thereof.

13 Claims, 20 Drawing Sheets

(56) References Cited

OTHER PUBLICATIONS

Hadano et al., Nat Genet., 2001, vol. 29, pp. 166-173, abstract.
Hamida et al., Brain, 1990, vol. 113, pp. 347-363, abstract.
Kappos et al., NEJM, 2006, vol. 355, pp. 1124-1140.
Kullberg et al., Brain Res, 2001, vol. 899, pp. 169-186, abstract.
Mohan et al., Haematologica, 2009, vol. 94, pp. 1407-1414.
Nicols, J Neurobiol. Sep. 15, 1999;40(4):585-601.
Rafii et al., BMC Med, 2009, vol. 7, pp. 7-10.
Rosen et al., Nature, 1993, vol. 362, pp. 59-62, abstract.
Shimizu et al., Circulation, 2005, vol. 111, pp. 222-229.
Shy Me, et al., "Motor neuron disease and plasma cell dyscrasia," Neurology, 36(11): 1429-1436 (1986) Abstract.
Siddique, T., et al., "Familial amyotrophic lateral sclerosis," J. Neural Transm. Suppl., 49: 219-33(1997) Abstract.
Siddique, T. and A. Hentati, "Familial amyotrophic lateral sclerosis," Clin. Neurosci., 3(6): 338-47(1995) Abstract.
Siddique, T., et al., "Linkage of a gene causing familial amyotrophic lateral sclerosis to chromosome 21 and evidence of genetic-locus heterogeneity," N. Engl. J. Med., 324(20): 1381-84 (1991).
Yang, Y., et al., "The gene encoding alsin, a protein with three guanine-nucleotide exchange factor domains, is mutated in a form of recessive amyotrophic lateral sclerosis," Nat. Genet., 29(2): 160-65 (2001) Abstract.
Younger DS, et al., "Motor neuron disease and amyotrophic lateral sclerosis: relation of high CSF protein content to paraproteinemia and clinical syndromes," Neurology, 40(4): 595-599 (1990) Abstract.
Yu, W.H., et al., "Phenotypic and functional changes in glial cells as a function of age," Neurobiol. Aging, 23(1): 105-15 (2002) Abstract.

* cited by examiner

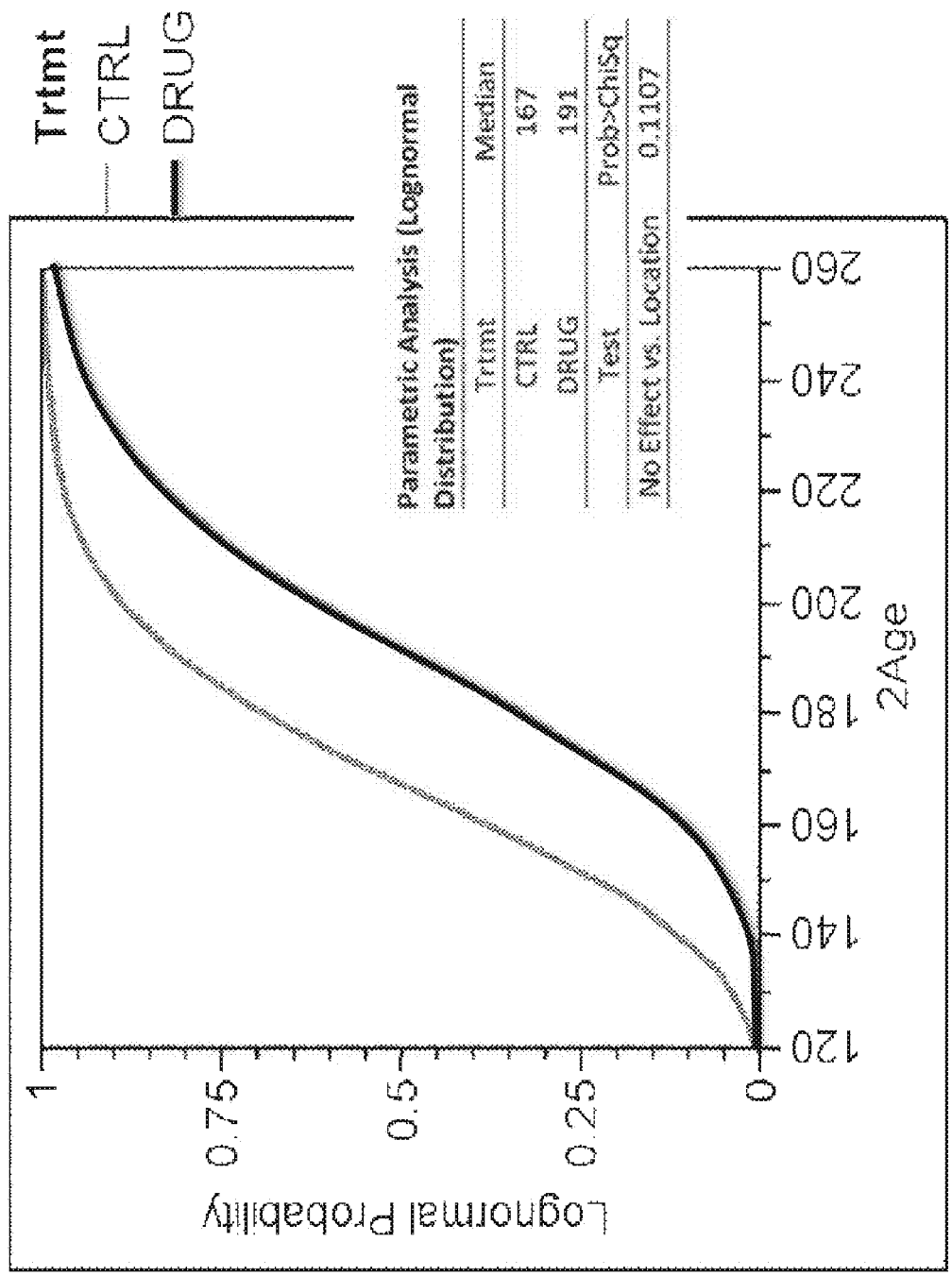

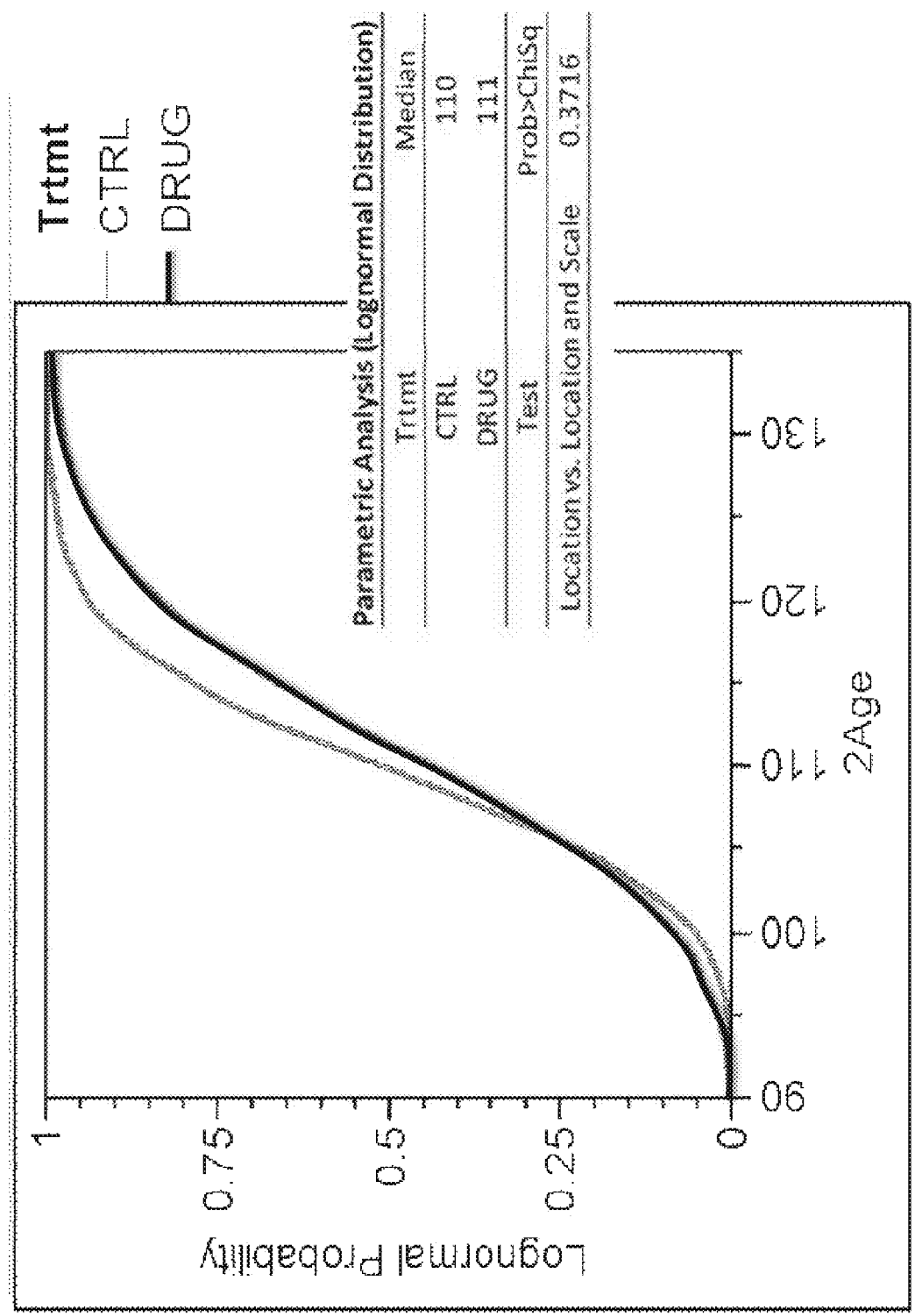

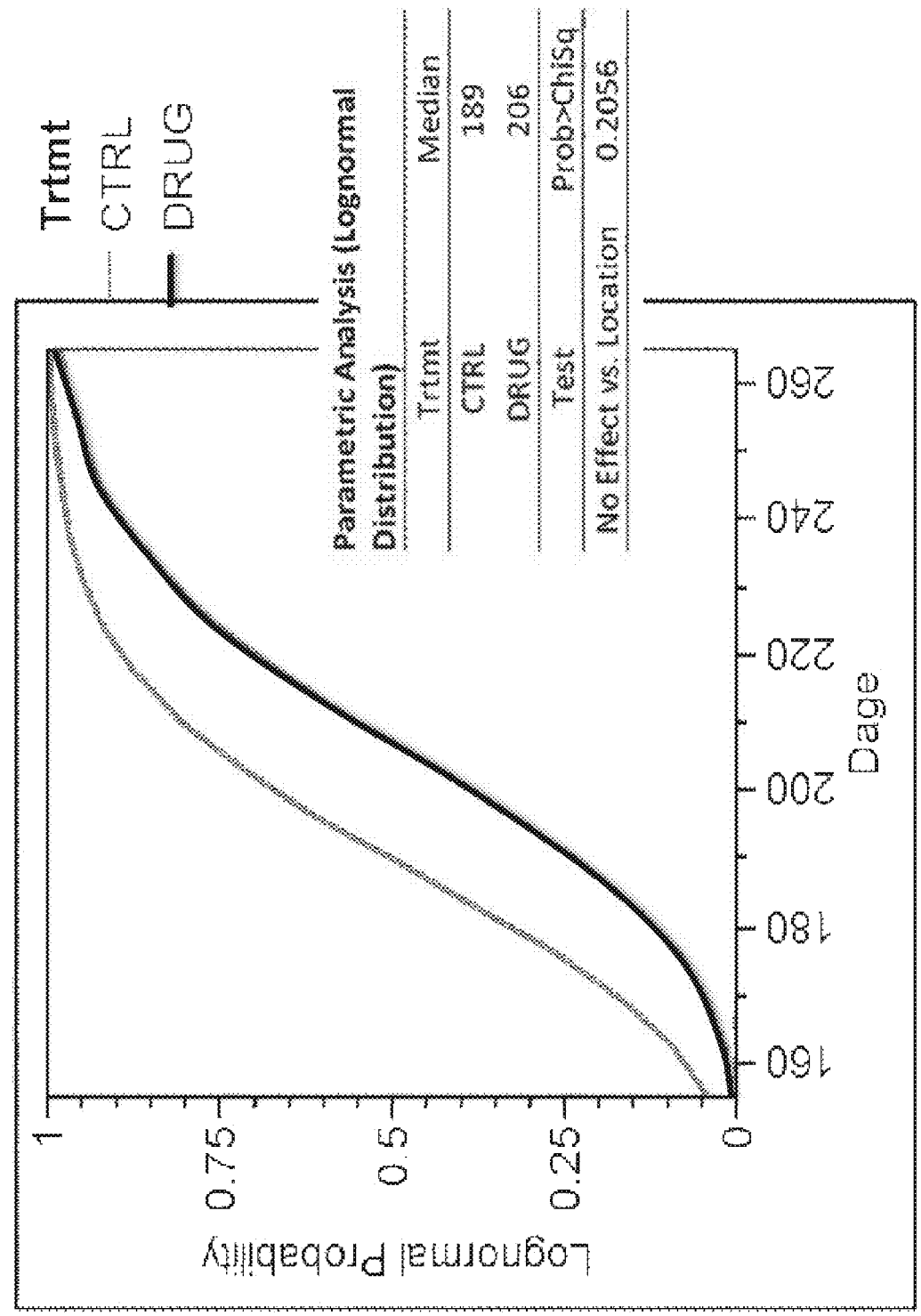

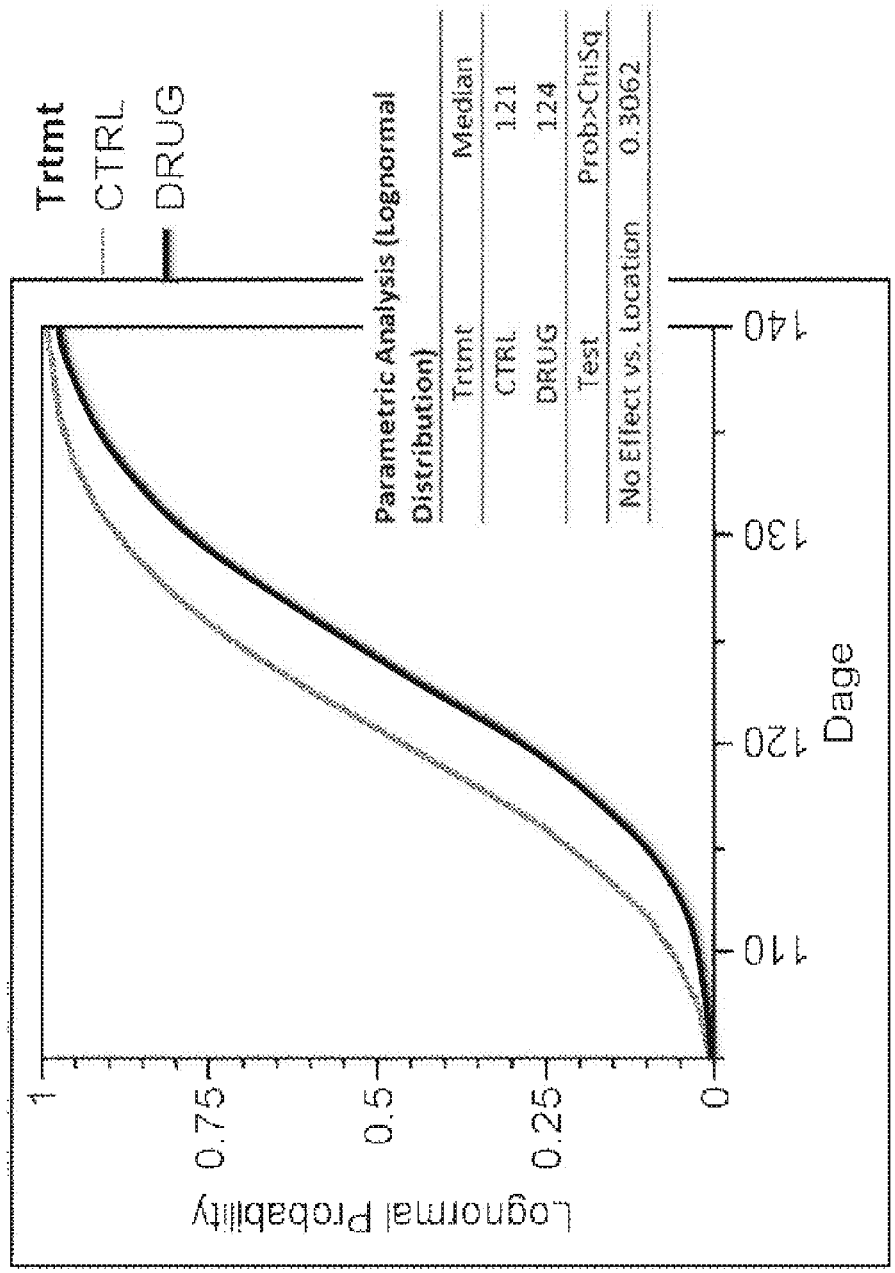

FIGURE 8C

| | Haz. Ratio | Std. Err. | z | P>z | [95% Conf. Interval] |
|---|---|---|---|---|---|
| _t | | | | | |
| trtmt_n | 0.51 | 0.20 | -1.68 | 0.0930 | 0.23 1.12 |
| sog | 0.00 | 0.00 | -2.00 | 0.0460 | 0.00 0.84 |

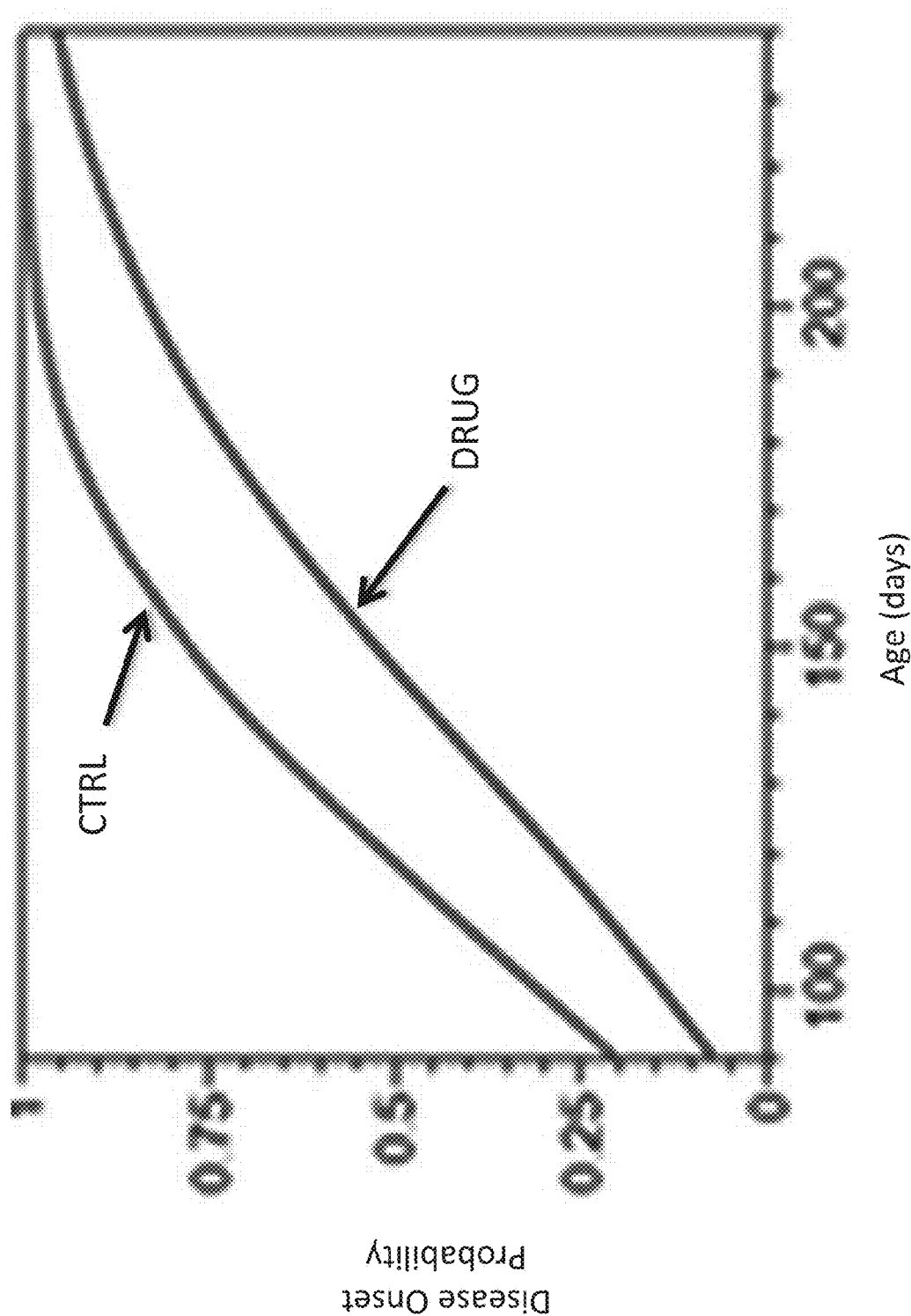

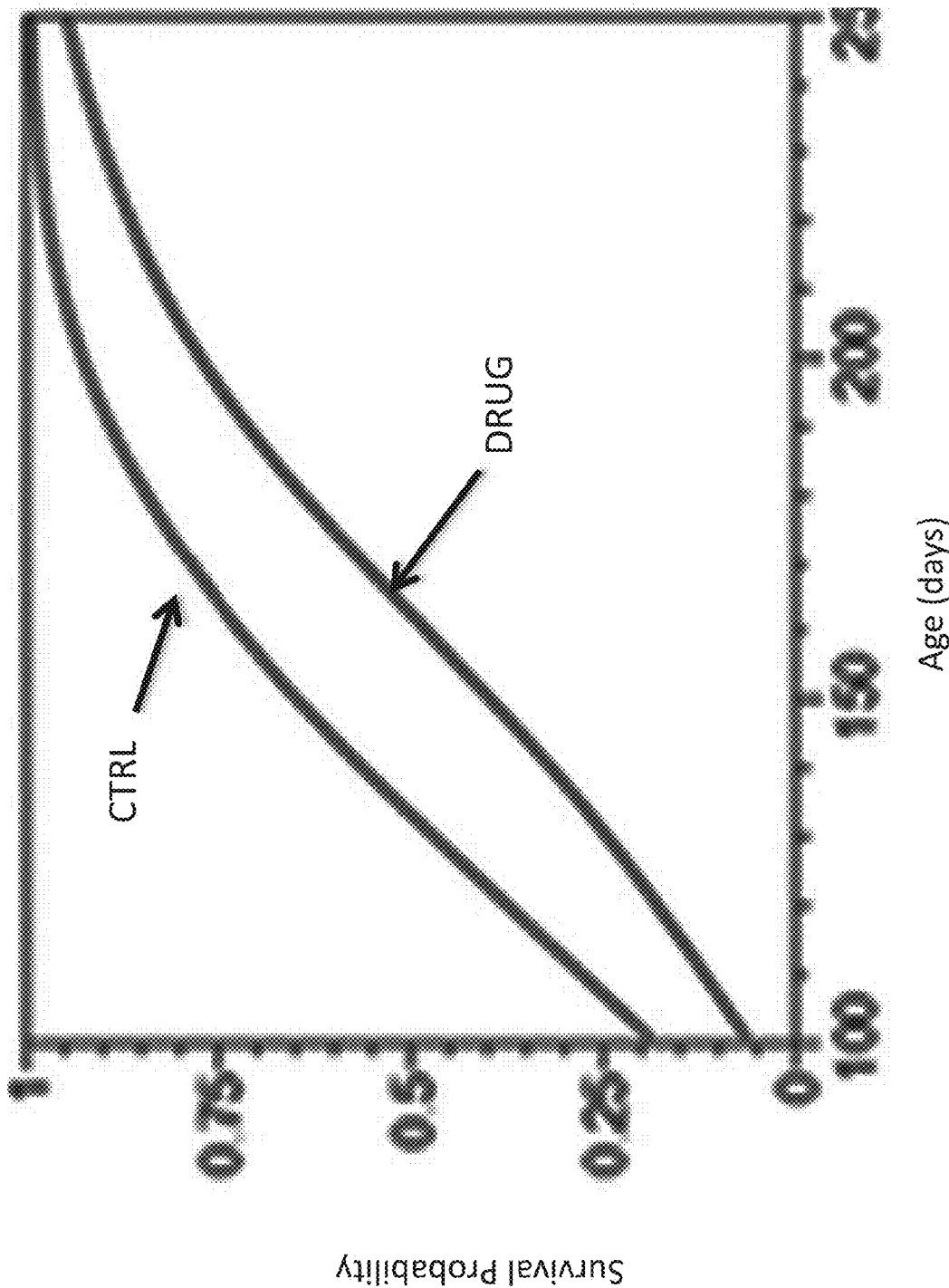

FIGURE 9C

| Source | nPam | Df | ChiSquare | Prob>ChiSq |
|---|---|---|---|---|
| Trtmt | 1 | 1 | 5.026 | 0.025 |

Estimates of Time Quantile

| Trtmt | Time (d) | Lower 95% | Upper 95% |
|---|---|---|---|
| CTRL | 123 | 108 | 141 |
| DRUG | 155 | 135 | 179 |

| Df | ChiSquare | Prob>ChiSq |
|---|---|---|
| 2 | 8.621 | 0.0134 |

FIGURE 9D

| Source | nParm | Df | ChiSquare | Prob>ChiSq |
|---|---|---|---|---|
| Trtmt | 1 | 1 | 3.894 | 0.049 |

Estimates of Time Quantile

| Trtmt | Time (d) | Lower 95% | Upper 95% |
|---|---|---|---|
| CTRL | 140 | 122 | 159 |
| DRUG | 169 | 147 | 193 |

| Df | ChiSquare | Prob>ChiSq |
|---|---|---|
| 2 | 7.5488 | 0.023 |

TARGETING OF T-LYMPHOCYTES TO TREAT AMYOTROPHIC LATERAL SCLEROSIS

CROSS-REFERENCE TO RELATED APPLICATIONS

This application claims priority to U.S. Provisional Application Ser. No. 61/564,515 filed Nov. 29, 2011, herein incorporated by reference in its entirety.

BACKGROUND OF THE INVENTION

The technical field of this invention is the treatment of neurodegenerative and neuromuscular disorders and, in particular, the treatment of Amyotrophic Lateral Sclerosis (ALS).

ALS is a progressive neurological disorder characterized by muscle fiber atrophy resulting from the degeneration of motor neurons in the spinal column and brain. ALS affects approximately 30,000 US citizens, with only ≈10% of cases being classified as the familial form of ALS. In a subset of familial patients with mutations in the metabolic enzyme superoxide dismutase 1 (SOD1), the pathological progression may be attributed to an unknown gain of function associated with a mutant form of the enzyme, i.e., is SOD1 dependant. However in the majority of ALS cases the SOD1 gene contains no mutations, the activity of the SOD1 enzyme is normal, and the mechanism of disease pathology is unknown, i.e., not SOD1 dependent. Therefore, the remaining 90% of ALS cases are classified as sporadic cases, with no well-characterized genetic component or causal agent.

While the role of infiltrating lymphocytes is poorly understood, recent work suggests that infiltrating T cell populations are neuroprotective. In recent studies mSOD1 mice were crossed with RAG2$^{-/-}$ mice, which have no mature T or B cells, (mSOD1/RAG2$^{-/-}$) or with CD4$^{-/-}$ mice which lack CD4$^+$ T cells. Both the mSOD1/RAG2$^{-/-}$ and mSOD1/CD4$^{-/-}$ transgenic mice have a significantly shorter lifespan (16 vs. 24 weeks) suggesting a neuroprotective effect of infiltrating lymphocytes.

However, it has recently been discovered that certain populations of infiltrating lymphocytes are not neuroprotective but rather are contributing factors in the progression of neurological disorders. In particular, infiltration of CD8-positive (CD8+) T cells have been found to contribute to progressive neurodegeneration, especially in diseases such as Amyotrophic Lateral Sclerosis (ALS).

SUMMARY OF THE INVENTION

Methods and compositions are disclosed that relate to the treatment of neurodegenerative and neuromuscular disorders characterized by activation of antigen-presenting cells or changes in cytotoxic T cell populations and, in particular the treatment of Amyotrophic Lateral Sclerosis (ALS).

In one aspect, methods and therapeutic compositions for treating ALS by administering a compound are disclosed. The compound can belong to a class of sphingosine1-phosphate receptor modulators and can be defined by the general Formula (I):

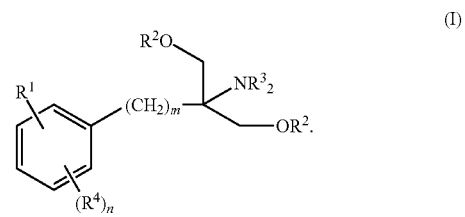

In one embodiment, $R^1$ can be a straight or branched $C_6$-$C_{20}$ alkyl, $C_6$-$C_{20}$ alkenyl, $C_6$-$C_{20}$ alkynyl, or one or more of the carbon atoms in $R^1$ can be substituted with a moiety selected from O, S, S(O), $SO_2$, $NH_2$, $N(R_2)_2$, and phenyl. $R^1$ can also be optionally substituted with one or more of $C_1$-$C_6$ alkoxy, $C_1$-$C_6$ alkenyloxy, $C_1$-$C_6$ alkynyloxy, $C_1$-$C_6$ aralkyloxy, acyl, $C_1$-$C_6$ alkylamino, $C_1$-$C_6$ alkylthio, acylamino, $C_1$-$C_6$ alkoxycarbonyl, $C_1$-$C_6$ alkoxycarbonylamino, acyloxy, $C_1$-$C_6$ alkylcarbamoyl, nitro, halogen, amino, hydroxy or carboxy. Each $R^2$ and $R^3$ can be independently H, P(O)(OH)$_2$, acyl, alkoxycarbonyl, or a $C_1$-$C_6$ alkyl. In exemplary embodiments, each $R_2$ is OH, both $R_2$ are P(O)(OH)$_2$, or one $R_2$ is OH and the other $R_2$ is P(O)OH)$_2$. Each $R^4$ can be independently a halogen, $CF_3$, OH, a $C_1$-$C_4$ alkyl, or a $C_1$-$C_4$ alkyloxy. Also, n can be 0, 1, or 2 and m can be 2, 3, or 4. In another embodiment, compounds where $R^1$ is an unsubstituted straight or branched $C_6$-$C_{20}$ alkyl, $C_6$-$C_{20}$ alkenyl, $C_6$-$C_{20}$ alkynyl, and $C_8$ alkyl.

The compound can also be defined by the general Formula (II):

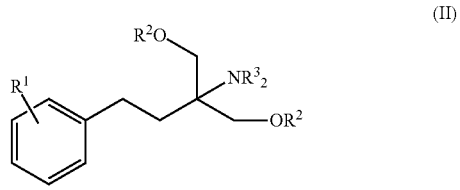

In another embodiments, the compound can be a pharmaceutically acceptable salt, hydrate, or solvate thereof. In an exemplary embodiment, the compound is a chloride salt, hydrochloride salt, or a phosphate salt.

In one exemplary embodiment, the compound is fingolimod (FTY720) or 2-amino-2-(4-octylphenethyl)propane-1,3-diol. In another exemplary embodiment, the compound is 2-amino-2-[2-[2-chloro-4-(3-phenylmethoxyphenyl)sulfanylphenyl]ethyl]propane-1,3-diol (KRP-203).

Methods and therapeutic compositions are also disclosed for modulating or ameliorating the neuroinflammatory processes associated with T-lymphocytes, including one or more of CD8+, CD4+, and CD45R+ T cell populations in neurodegenerative or neuromuscular disorders, and particularly Amyotrophic Lateral Sclerosis.

In one aspect, administration of the compound can inhibit macrophage accumulation. The accumulation can be localized in the axons of nerves innervating the skeletal muscle. The compound can inhibit accumulation of at least 50% compared to the macrophage population prior to administering the compound, in particular by inhibiting CD11b positive macrophage. In another aspect, administration of the compound can reduce lymphocyte proliferation. The reduction can include reducing the concentration of one or more of CD8+ T cell, CD4+ T cell, and CD45R+ T cell in whole blood by at least 30 percent compared to the concentration in whole blood prior to administering the compound or reducing the concentration of one or more of CD8+ T cell, CD4+ T cell, and CD45R+ cell in spinal fluid by at least 30 percent compared to the concentration in whole blood prior to administering the compound.

In one embodiment this can be achieved through sequestering, neutralizing or depleting cytotoxic T cells by administering a sphingosine1-phosphate receptor modulator such as the S1P modulator described herein below as formula (I).

In another embodiments, the compound can be formulated with a pharmaceutically acceptable diluent, adjuvant, or carrier. The compound can be formulated for oral administration, a single daily dose, and/or a dosage between 0.1 to 150 mg. The compositions can be administered as a single dose or in multiple doses and can further include a pharmaceutically acceptable carrier.

In other embodiments, methods for decreasing macrophage accumulation on peripheral axons in a subject having a neurodegenerative or neuromuscular disorder as well as methods for treating neurodegenerative and neuromuscular disorders are disclosed. The neurodegenerative and neuromuscular disorders are characterized by activation of antigen-presenting cells or show changes in cytotoxic T cell populations by blocking of lymphocyte proliferation out of the diseased tissue. These indications include, but are not limited to, Alzheimer's Disease, Parkinson's Disease, Myasthenia Gravis, Multifocal Motor Neuropathy, Primary Lateral Sclerosis, Spinal Muscular Atrophy, Kennedy's Disease, and Spinocerebellar Ataxia.

BRIEF DESCRIPTION OF THE DRAWINGS

A detailed description of various embodiments is provided herein below with reference, by way of example, to the following drawings. The skilled person in the art will understand that the drawings, described below, are for illustration purposes only. The drawings are not intended to limit the scope of the applicant's teachings in any way.

FIGS. 7A, 7B, 7C, and 7D are charts showing symptomatic neurological disease progression in untreated SOD1 mice and SOD1 fingolimod treated mice. FIGS. 7A and 7C show the results for SOD1 mice having a low number (14-20) of copies of the transgene. FIGS. 7B and 7D show the results for SOD1 mice having a high number (20-25) copies of the transgene. Neurological disease progression was defined as the average neurological score over time for male SOD1 mice. For each chart, the lower line represents the SOD1 fingolimod treated mice; the upper line (i.e., having lower probability at each age in days, $D_{age}$) represents the untreated SOD1 mice.

FIG. 8C provides a table with the Cox Proportional Hazards analysis from FIGS. 8A and 8B.

FIG. 9A is a chart showing disease onset probability as calculated by the Weibull method versus time in untreated SOD1 mice and SOD1 fingolimod treated mice. The right line represents the SOD1 fingolimod treated mice; the left line represents the untreated SOD1 mice.

FIG. 9B is a chart showing survival as calculated by the Weibull method versus time in untreated SOD1 mice and SOD1 fingolimod treated mice. The right line represents the SOD1 fingolimod treated mice; the left line represents the untreated SOD1 mice.

FIG. 9C is a table showing the Weibull analysis of the data presented in FIG. 9A FIG. 9D is a table showing the Weibull analysis of the data presented in FIG. 9B.

DETAILED DESCRIPTION

Figure 1A:
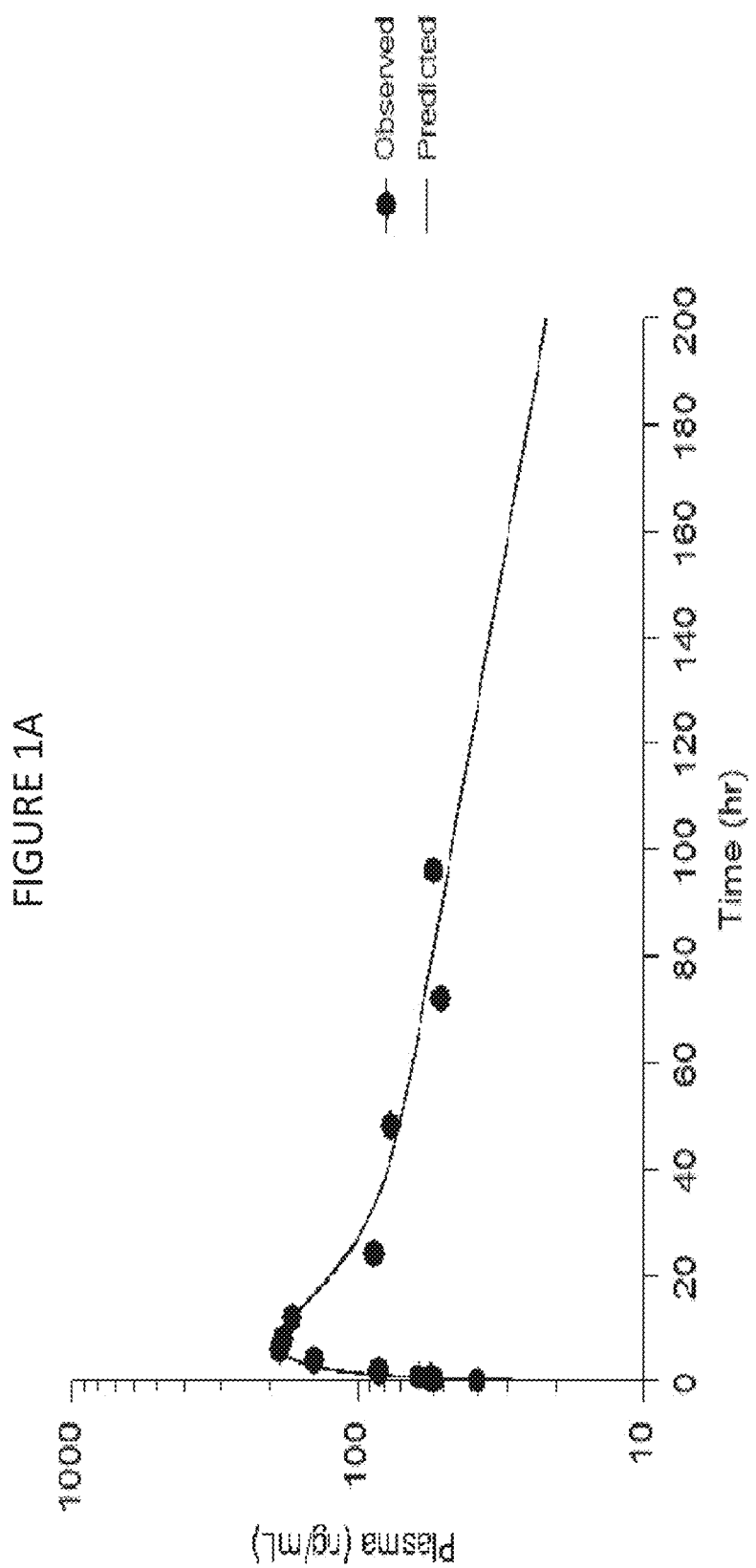
FIG. 1A is a chart showing the plasma pharmacokinetic profile for fingolimod in male SOD1 mice after a single IP bolus 6.7 mg/kg. The plasma half-life is 31.4 hours and the plasma $C_{max}$ is 185 ng/mL.

The following abbreviations are used throughout the specifications and known to those skilled in the art: ALS (amyotrophic lateral sclerosis); SOD1 (super oxide dismutase-1); TCR (T cell receptor); MHC (major histocompatibility complex); APC (antigen presenting cell); CD8 (a cell surface antigen on certain T cells), FACS (fluorescence activated cell sorting).

In the description that follows, and in documents incorporated by reference, a number of terms are used extensively.

The following definitions are provided to facilitate understanding of the methods and compositions disclosed herein.

As used herein, the term "subject" is a human or other animal, having a neurological disorder. In some embodiments, the subjects are mammals. Examples of subjects can include, but are not limited to, humans, horses, monkeys, dogs, cats, mice, rates, cows, pigs, goats and sheep. In some embodiments, "subjects" are generally human patients having ALS.

As used herein, a "therapeutic conjugate agent" is a molecule or atom, which is conjugated to a composition to produce a conjugate which is useful for therapy. These can be active when given unconjugated, such as with $^{131}$I in thyroid neoplasm, and various cytotoxic drugs in cancer, autoimmune diseases, graft versus host disease, and in the immunosuppression induced for organ transplantation, etc. Examples of therapeutic conjugate agents include a therapeutic radionuclide, a boron compound, an immunomodulator, a hormone, a hormone antagonist, an enzyme, oligonucleotides, an enzyme inhibitor, a photoactive therapeutic agent, a cytotoxic agent, and an angiogenesis inhibitor, and a combination thereof, and further described, for example, in US Published Application no. 2004/0057902.

A diagnostic/detection agent can be a molecule or atom which is administered conjugated to the composition, and can be useful in diagnosing a disease by locating the cells containing the antigen. Useful diagnostic/detection agents can include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI), as well as for ultrasound and computed tomography.

The term "treatment" or "treating" as used herein is intended to encompass preventing the onset, slowing the progression, reversing or otherwise ameliorating a neurodegenerative and neuromuscular disorders. In one exemplary embodiment, the neurodegenerative disease being treated is ALS.

The term "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The term "about" or "approximately" means within an acceptable error range for the particular value as determined by one of ordinary skill in the art, which will depend in part on how the value is measured or determined—e.g., the limitations of the measurement system, or the degree of precision required for a particular purpose. For example, "about" can mean within 1 or more than 1 standard deviations, as per the practice in the art. Alternatively, "about" can mean a range of up to 20%, preferably up to 10%, more preferably up to 5%, and more preferably still up to 1% of a given value. Where particular values are described in the application and claims, unless otherwise stated, the term "about" meaning within an acceptable error range for the particular value should be assumed.

As used herein and in the appended claims, the singular forms "a," "an," and "the," include plural referents unless the context clearly indicates otherwise. Thus, for example, reference to "a molecule" includes one or more of such molecules and reference to "the method" includes reference to equivalent steps and methods known to those of ordinary skill in the art that could be modified or substituted for the methods described herein.

Amyotrophic Lateral Sclerosis

Amyotrophic Lateral Sclerosis (ALS) is a neurodegenerative condition in which patients progressively lose all motor function. Evidence is accumulating that as a result of the aging process the body increasingly loses the ability to adequately degrade mutated or misfolded proteins. The proteasome is the piece of biological machinery responsible for most normal degradation of proteins inside cells. Age related loss of function or change of function of the proteasome is now thought to be at the heart of many neurodegenerative conditions, including Alzheimer's disease, Parkinson's disease, Huntington's disease, and ALS.

ALS, also called Lou Gehrig's disease, affects the motor neurons of the cortex, brain stem and spinal cord. (Hirano, A., "Neuropathology of ALS: an overview," *Neurology*, 47(4 Suppl. 2): S63-6 (1996)). ALS affects approximately 30,000 Americans with nearly 8,000 deaths reported in the US each year. ALS remains one of the most devastating diseases and advances in treatment are desperately needed.

The cardinal feature of ALS is the loss of spinal motor neurons, which causes the muscles under their control to weaken and waste away leading to paralysis. ALS has both familial (5-10%) and sporadic forms and the familial forms have now been linked to several distinct genetic loci (Deng, H. X., et al., "Two novel SOD1 mutations in patients with familial amyotrophic lateral sclerosis," *Hum. Mol. Genet.*, 4(6): 1113-16 (1995); Siddique, T. and A. Hentati, "Familial amyotrophic lateral sclerosis," *Clin. Neurosci.*, 3(6): 338-47 (1995); Siddique, T., et al., "Familial amyotrophic lateral sclerosis," *J. Neural Transm. Suppl.*, 49: 219-33(1997); Ben Hamida, et al., "Hereditary motor system diseases (chronic juvenile amyotrophic lateral sclerosis). Conditions combining a bilateral pyramidal syndrome with limb and bulbar amyotrophy," *Brain*, 113(2): 347-63 (1990); Yang, Y., et al., "The gene encoding alsin, a protein with three guanine-nucleotide exchange factor domains, is mutated in a form of recessive amyotrophic lateral sclerosis," *Nat. Genet.*, 29(2): 160-65 (2001); Hadano, S., et al., "A gene encoding a putative GTPase regulator is mutated in familial amyotrophic lateral sclerosis 2," *Nat. Genet.*, 29(2): 166-73 (2001)). About 15-20% of familial cases are due to mutations in the gene encoding Cu/Zn superoxide dismutase 1 (SOD1) (Siddique, T., et al., "Linkage of a gene causing familial amyotrophic lateral sclerosis to chromosome 21 and evidence of genetic-locus heterogeneity," *N. Engl. J. Med.*, 324(20): 1381-84 (1991); Rosen, D. R., et al., "Mutations in Cu/Zn superoxide dismutase gene are associated with familial amyotrophic lateral sclerosis." Nature, 362(6415): 59-62 (1993)).

Although ALS is characterized by loss of motor neurons in the spinal cord resulting in muscle atrophy, the disease also manifests itself with changes in axon transport, protein aggregation, excitotoxicity, astrocytosis, mitochondrial dysfunction, microglial activation and synaptic remodeling. Microglial activation, astrocytosis and the presence of infiltrating inflammatory cells from outside the central nervous system have been well described. There is accumulation of IgG immunoreactive deposits in the spinal cord of ALS patients, infiltration of lymphocytes, dendritic cells, monocytes, and macrophages into the spinal cord in ALS.

Early symptoms of ALS include increasing muscle weakness, particularly in the arms and legs, and in the muscles associated with speech, swallowing and breathing. Symptoms of weakness and muscle atrophy usually begin asymmetrically and distally in one limb, and then spread within the neuroaxis to involve contiguous groups of motor neurons. Symptoms can begin either in bulbar or limb muscles. Clinical signs of both lower and upper motor neuron involvement are required for a definitive diagnosis of ALS. Respiration is usually affected late in limb onset patients, but occasionally can be an early manifestation in patients with bulbar onset symptoms.

While ALS is a primary neurological disease, as is multiple sclerosis (MS), the two diseases have very distinct pathology and disease progression. While ALS is a disease primarily of the nerve cells, MS is a disease of myelin. The myelin surrounds the axons, or the long process of the nerve cell. Since myelin occurs throughout the nervous system, lesions can be and typically are at multiple sites. MS, however, affects central myelin, not the myelin of peripheral nerves. Thus, the symptoms of MS are specifically of a central nervous system disorder. Another distinguishing feature of MS pathology is inflammation of the perivascular inflammatory cells whereas inflammation is not a symptom of ALS, either as a primary or a secondary phenomenon. Life expectancy may be shortened in some patients with MS, but this shortening varies greatly, and in some cases, the affliction is so mild that they never come to the attention of a physician.

Presently, there is no cure for ALS, nor is there a therapy that has been proven effective to prevent or reverse the course of the disease. Several drugs have recently been approved by the Food and Drug Administration (FDA). To date, attempts to treat ALS have involved treating neuronal degeneration with long-chain fatty alcohols which have cytoprotective effects (See U.S. Pat. No. 5,135,956); or with a salt of pyruvic acid (See U.S. Pat. No. 5,395,822); and using a glutamine synthetase to block the glutamate cascade (See U.S. Pat. No. 5,906,976). For example, Riluzole™, a glutamate release inhibitor, has been approved in the U.S. for the treatment of ALS, and appears to extend the life of at least some patients with ALS. However, some reports have indicated that even though Riluzole™ therapy can prolong survival time, it does not appear to provide an improvement of muscular strength in the patients. Therefore, the effect of Riluzole™ is limited in that the therapy does not modify the quality of life for the patient (Borras-Blasco et al., *Rev. Neurol.*, 27: 1021-1027 (1998)).

Although the etiology of the disease is unknown, the dominant theory is that neuronal cell death in ALS is the result of over-excitement of neuronal cells due to excess extracellular glutamate. Additionally, although ALS is not considered an autoimmune disease, recent studies implicate inflammation in disease pathogenesis. Activated microglia and expression of inflammatory mediators are observed in ALS spinal cord and a significant increase in free radical damage is seen in sera and cerebrospinal fluid of ALS patients. In aging, microglia, the resident macrophages of the central nervous system are shown to become activated (Nichols, N. R., "Glial responses to steroids as markers of brain aging," *J. Neurobiol.*, 40(4): 585-601 (1999); Yu, W. H., et al., "Phenotypic and functional changes in glial cells as a function of age," *Neurobiol. Aging*, 23(1): 105-15 (2002)). Activation of microglia with aging both increases susceptibility to biochemical stress as well as to neurodegeneration (Nichols, N. R., "Glial responses to steroids as markers of brain aging," *J. Neurobiol.*, 40(4): 585-601 (1999); Kullberg, S., et al., "Microglial activation, emergence of ED1-expressing cells and clusterin upregulation in the aging rat CNS, with special reference to the spinal cord," *Brain Res.*, 899(1-2): 169-86 (2001)). Increased involvement of immune dysfunction in ALS patients is shown by higher incidence of autoimmune thyroid diseases (21%), paraproteinemias (5.6%), monoclonal immunoglobulin detection (60%), and co-association of lymphoma and MND (Gordon P H, et al., "Lymphoproliferative disorders and motor neuron disease: an update," *Neurology*, 50(2): 576 (1997); Duarte F, et al., "Quantitative analysis of monoclonal immunoglobulins in serum of patients with amyotrophic lateral sclerosis," *J. Neurol. Sci.*, 104(1): 88-91 (1991); Shy M E, et al., "Motor neuron disease and plasma cell dyscrasia," *Neurology*, 36(11): 1429-1436 (1986); Sriram S, et al., "Indictment of the microglia as the villain in multiple sclerosis," *Neurology*, 48(2): 464-70 (1997); Younger D S, et al., "Motor neuron disease and amyotrophic lateral sclerosis: relation of high CSF protein content to paraproteinemia and clinical syndromes," *Neurology*, 40(4): 595-599 (1990)).

A mouse model for ALS is the SOD1-G93A mouse. The SOD1-G93A mouse model is a mouse that carries 25 copies of the human G93A SOD mutation and is driven by the endogenous promoter. Survival in the mouse is copy dependent. The high copy G93A has a median survival of around 128 days. High molecular weight complexes of mutant SOD protein are seen in the spinal cord beginning around day 30. At day 60 reactive astrocytosis (GFAP reactive) are observed; activated microglia are observed from day 90 onwards. Studies by Gurney et al. showed that at day 90 reactive astrocytosis loses statistical significance while microglial activation is significantly elevated and continues to be elevated through the end stage of the disease. Many drugs that have shown efficacy in this model have moved forward into human clinical trials. Experience with riluzole, the only approved drug in the treatment of ALS, indicates that the mouse ALS model is a good predictor of clinical efficacy. Other drugs such as Creatine, Celebrex, Co-enzyme Q10 are under clinical evaluation based on studies in this model.

Sphingosine1-Phosphate Receptor Modulators

A class of sphingosine1-phosphate receptor modulators according to the invention can be defined by the compound of Formula (I):

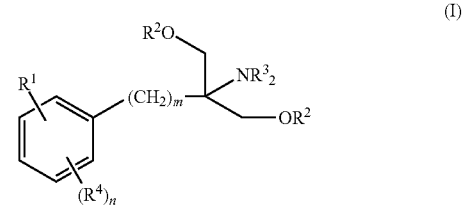

In some embodiments, $R^1$ may be a straight or branched $C_6$-$C_{20}$ alkyl, $C_6$-$C_{20}$ alkenyl, $C_6$-$C_{20}$ alkynyl, or wherein one or more of the carbon atoms in $R^1$ may be substituted with a moiety selected from O, S, S(O), $SO_2$, $NH_2$, $N(R_2)_2$, and phenyl, and wherein $R^1$ is optionally substituted with one or more of $C_1$-$C_6$ alkoxy, $C_1$-$C_6$ alkenyloxy, $C_1$-$C_6$ alkynyloxy, $C_1$-$C_6$ aralkyloxy, acyl, $C_1$-$C_6$ alkylamino, $C_1$-$C_6$ alkylthio, acylamino, $C_1$-$C_6$ alkoxycarbonyl, $C_1$-$C_6$ alkoxycarbonylamino, acyloxy, $C_1$-$C_6$ alkylcarbamoyl, nitro, halogen, amino, hydroxy or carboxy; each $R^2$ and $R^3$ may be independently a H, $P(O)(OH)_2$, acyl, alkoxycarbonyl, or a $C_1$-$C_6$ alkyl; each $R^4$ may be independently a halogen, $CF_3$, OH, a $C_1$-$C_4$ alkyl, or a $C_1$-$C_4$ alkyloxy; n may be 0, 1, or 2; and m may be 2, 3, or 4.

In some embodiments, $R^1$ is an unsubstituted straight or branched $C_6$-$C_{20}$ alkyl, $C_6$-$C_{20}$ alkenyl, or $C_6$-$C_{20}$ alkynyl. In some embodiments, m is 1, 2, or 3. In some embodiments, m is 2. In some embodiments, n is 0 or 1. In some embodiments, n is 0. In yet other embodiments, $R^1$ is an unsubstituted straight chain $C_8$ alkyl. In some embodiments, $R^1$ is an unsubstituted straight chain $C_8$ alkyl. In some embodiments, $R_1$ is a $C_6$-$C_{20}$ alkyl wherein one or more of the carbon atoms in $R^1$ is substituted with a moiety selected from O, S, and phenyl, n is 1, and $R_4$ is a halogen. In some embodiments, each $R^2$ and $R^3$ are each H.

In some embodiments, the sphingosine1-phosphate receptor modulators can be defined by the compounds of Formula (II):

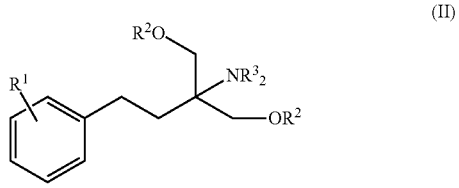

In some embodiments, $R^1$ may be a straight or branched $C_6$-$C_{20}$ alkyl, $C_6$-$C_{20}$ alkenyl, $C_6$-$C_{20}$ alkynyl, or wherein one or more of the carbon atoms in $R^1$ may be substituted with a moiety selected from O, S, S(O), $SO_2$, $NH_2$, $N(R_2)_2$, and phenyl, and wherein $R^1$ is optionally substituted with one or more of $C_1$-$C_6$ alkoxy, $C_1$-$C_6$ alkenyloxy, $C_1$-$C_6$ alkynyloxy, $C_1$-$C_6$ aralkyloxy, acyl, $C_1$-$C_6$ alkylamino, $C_1$-$C_6$ alkylthio, acylamino, $C_1$-$C_6$ alkoxycarbonyl, $C_1$-$C_6$ alkoxycarbonylamino, acyloxy, $C_1$-$C_6$ alkylcarbamoyl, nitro, halogen, amino, hydroxy or carboxy; each $R^2$ and $R^3$ may be independently a H, $P(O)(OH)_2$, acyl, alkoxycarbonyl, or a $C_1$-$C_6$ alkyl. In an exemplary embodiment, $R^1$ is an unsubstituted straight or branched $C_6$-$C_{20}$ alkyl, $C_6$-$C_{20}$ alkenyl, or $C_6$-$C_{20}$ alkynyl. In another exemplary embodiment, $R^1$ is an unsubstituted straight chain $C_8$ alkyl. In some embodiments, $R_1$ is a $C_6$-$C_{20}$ alkyl wherein one or more of the carbon atoms in $R^1$ is substituted with a moiety selected from O, S, and phenyl.

One exemplary sphingosine1-phosphate receptor modulator can be fingolimod (FTY720) or 2-amino-2-(4-octylphenethyl)propane-1,3-diol:

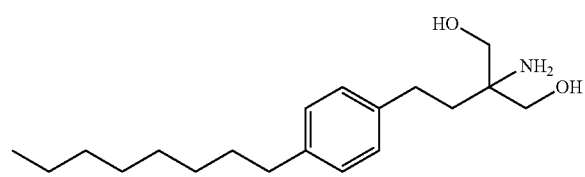 [SMILES: CCCCCCCCc1ccc(CCC(N)(CO)CO)cc1]

This compound, having a molecular weight of 343.9 g/mol, has been shown to be an effective immunosuppressant. Both the compounds and their synthesis are described in U.S. Pat. No. 5,604,229. Fingolimod is approved for use in the U.S. for treating multiple sclerosis and sold by Novartis Pharma as Gilenya® as an oral formulation. Fingolimod was derived from the fungus *Isaria sinclairii* and is a structural analogue of sphingosine, which is phosphorylated by sphingosine kinase in situ. After phosphorylation, fingolimod-P acts as a superagonist of the sphingosine-1-phosphate-1 receptor on thymocytes and lymphocytes and induces aberrant internalization of this receptor. Circulating lymphocytes are thus sequestered in the lymph nodes, reducing peripheral lymphocyte populations. The recirculation of lymphocytes to the central nervous system is also reduced. However, lymphocytes in secondary lymphoid organs and those remaining in blood continue to be functional. (Kappos et al., *N Engl J Med.* 2006 Sep. 14; 355(11):1124-40.)

The sphingosine1-phosphate receptor modulators also include pharmaceutically acceptable salts, hydrates, or solvates thereof, as well as functional derivatives and analogs. Pharmaceutically acceptable salts, as well as pharmaceutical formulations of the sphingosine 1-phosphate receptor modulators, are also provided herein. Suitable salts may include, but are not limited to, salts formed with inorganic acids (for example, hydrochloric acid, hydrogen bromide, sulfuric acid, phosphoric acid, nitric acid, and the like), salts formed with organic acids such as acetic acid, oxalic acid, tartaric acid, succinic acid, malic acid, ascorbic acid, benzoic acid, tannic acid, palmitic acid, polyglutamic acid, naphthalene sulfonic acid, naphthalene disulfonic acid and polygalacturonic acid, phosphorylated derivatives, salts thereof. In an exemplary embodiment, the sphingosine1-phosphate receptor modulator is the hydrochloride salt of fingolimod.

A "derivative" or "analog" is defined as a sphingosine1-phosphate receptor modulator which has been subjected to chemical modification. Derivatization may include the substitution of certain chemical groups to the sphingosine1-phosphate receptor modulator. Such derivatizations are known from the state of the art. The derivatives and analogs maintain the biological activity of the sphingosine1-phosphate receptor modulator and function in a similar manner, but can offer advantages to the compound, such as a longer life, resistance to decomposition or increased activity. In an exemplary embodiment, the sphingosine1-phosphate receptor modulator is the phosphorylated derivative of fingolimod.

Another exemplary embodiment, the sphingosine1-phosphate receptor modulator is 2-amino-2-[2-[2-chloro-4-(3-phenylmethoxyphenyl)sulfanylphenyl]ethyl]propane-1,3-diol (KRP-203):

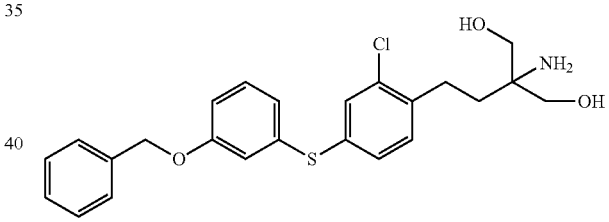

which is described in U.S. Pat. No. 7,456,157, Shimizu et al., *Circulation,* 2005, vol. 111, pp. 222-229, and Takahashi et al., *Transplant. Proc.,* 2005, vol. 37, pp. 143-145. The structural similarity between fingolimod and KRP-203 suggests that KRP-203 also sequesters peripheral lymphocytes and accelerates lymphocyte homing into the secondary lymphoid organ. KRP-203 has been shown to reduce the number of peripheral blood mononuclear cells (lymphocytes and monocytes) but not granulocytes and enhanced lymphocyte homing into peripheral lymph nodes.

Additional pharmaceutically acceptable salts and derivatives of fingolimod, KRP-203, or other sphingosine1-phosphate receptor modulators are also contemplated as useful compounds. For example, deuterated fingolimod as disclosed in U.S. Pat. Pub. 2009/0176744 may also be administered according to the methods herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate. Compounds described herein are optionally in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate The compounds described herein may be in crystalline or amorphous form, and may be in the form of a hydrate or a solvate. Several polymorphs of the crystalline form can be formulated and are also encompassed within the invention.

Treatment of ALS with a Sphingosine1-Phosphate Receptor Modulator

Without being limited to any particular mechanism of action, treatment with fingolimod appears to limit lymphocyte egress from secondary lymphoid tissue. Thus, circulating lymphocytes including CD4+, CD8+, and CD45RA+, CD3+ and CD45RO+ are sequestered in lymph nodes and the peripheral lymphocyte population and the recirculation of lymphocytes to the central nervous system is reduced. Reports consistently describe lymphopenia with fingolimod treatment (Tsunemi 2010 and Zemann 2006). One report indicates decreased lymphocyte population at least partially accounted for by large decreases of Cd4 and Cd8positive cells as determined by FACS analysis. While reports virtually all indicate reduced lymphocyte populations in whole blood, impact by fingolimod treatment on other lymphoid organs including thymus, lymph node, and spleen seem varied and nuanced. One published report suggests that lymphocyte population modulation in these organs is strongly influenced by the chemokine/chemokine receptor profile in the tissue (Yopp 2004). Another published report describes B cell recompartmentalization within the lymph node. Another report focuses on dendritic cells instead of T or B cells. This study demonstrates a large increase in circulating dendritic cells following fingolimod administration (Lan 2005, 2008).

The following examples and data demonstrate the presence of CD4+ and CD8+, T cells in peripheral blood of SOD1 animals. Based on FACS analysis, it is further demonstrated that treatment of SOD1 animals with fingolimod transiently depletes CD8+ and CD4+ T cells from peripheral blood. The examples and data disclosed herein also demonstrate that the treatment of the hSOD1 preclinical mouse model with fingolimod is effective. In one embodiment the concentration of one or more of CD8+ T cells, CD4+ T cells, or CD45R+ cells in whole blood is reduced by at least 30 percent compared to the concentration in whole blood prior to administering the compound. In another embodiment, the reduction is 40%, 50%, 60%, 70%, 80%, 90%, 95% or more. In another embodiment, the concentration of both CD8+ T cells, and CD4+ T cells in whole blood are reduced by at least 30%, 40%, 50%, 60%, 70%, 80%, 90%, 95% or more.

Inventors have determined that CD8+ and CD4+ T cells are also depleted from the spinal cord as well as from whole blood. In one embodiment the concentration of one or more of CD8+ T cells, CD4+ T cells, or CD45R+ cells in spinal fluid is reduced by at least 30 percent compared to the concentration in spinal fluid prior to administering the compound. In another embodiment, the reduction is 40%, 50%, 60%, 70%, 80%, 90%, 95% or more. In another embodiment, the concentration of both CD8+ T cells, and CD4+ T cells in spinal fluid are reduced by at least 30%, 40%, 50%, 60%, 70%, 80%, 90%, 95% or more.

Additionally, the inventors have determined treatment with sphingosine1-phosphate receptor modulators blocks macrophage infiltration into peripheral axons. Thus, in one embodiment, the macrophage accumulation on peripheral axons of a subject after administration of fingolimod is decreased compared to the macrophage accumulation levels prior to the administration of the compound. In one embodiment, macrophage accumulation on peripheral axons decreased by at least 50% compared to macrophage accumulation levels prior to the administration of the compound. In other embodiments, the macrophage infiltration is blocked by at least 60%, at least 70%, at least 80%, at least 90%, or at least 95%. In one embodiment, the macrophage accumulation level is measured one week, two weeks, three weeks, one month, two months, three months, or more after initiating administration of a sphingosine1-phosphate receptor modulator.

It has been suggested that the expression of the CD8a/CD8b heterodimer is restricted to T lymphocytes which matured in the thymus or in an extrathymic environment that had been influenced by thymus-initiated neuroendocrine signals. CD8 is an antigen coreceptor on the T-cell surface which interacts with MHC class I molecules on antigen-presenting cells or epithelial cells. It participates in T-cell activation through its association with the T-cell receptor complex and protein tyrosine kinase lck (p56 [lck]).

The effect of depleting cytotoxic CD8+ and/or CD4+ T cell populations with the compounds disclosed herein is to ameliorate disease in the mouse preclinical neurodegenerative ALS model. Depleting CD8+ and/or CD4+ cytotoxic T cells may be advantageous in other neurodegenerative and neuromuscular disease indications such as Alzheimer's Disease, Parkinson's Disease, Myasthenia Gravis, Multifocal Motor Neuropathy, Primary Lateral Sclerosis, Spinal Muscular Atrophy, Kennedy's Disease, and Spinocerebellar Ataxia. Thus, in one aspect, the compound can be administered to treat other neurodegenerative and neuromuscular disease indications.

Fingolimod may promote remeylination by oligodendrocytes after axonal injury. Miron et al. (*Ann Neurol.* 2008 January; 63(1):61-71) has hypothesized that fingolimod induces time-dependent modulation of S1P receptors on human oligodendroacyte progenitor cells with consequent functional responses that are directly relevant for the remyelination process. Fingolimod may also reduce monocyte infiltration into peripheral nerves. It was found to suppress paraparesis if administrated with immunization as well as reduced the severity and duration of experimental autoimmune neuritis. (Zhang, Z et al., *Exp Neurol.* 2008 Jan. 17). It has been theorized that cellular accumulation of fingolimod generates a reservoir in thymus and secondary lymphoid organs, leading to activation of sphingosine-1-phosphate within tissues. And thus, the accumulation of fingolimod in lymphoid tissues may promote its efficacy (Sensken et al., *J Pharmacol Exp Ther.* 2009 March; 328(3):963-9). Fingolimod has also been shown to be a CNS penetrant and localizes in the CNS white matter (Foster, C A et al., *J Pharmacol Exp*

Ther. 2007 November; 323(2):469-75) and to increase regulatory T cells (Zhang et al., *Exp Neurol.* 2009 March; 216(1): 75-82).

Pharmaceutical Compositions of Sphingosine1-Phosphate Receptor Modulators

The sphingosine1-phosphate receptor modulator may be administered as a pharmaceutically acceptable salt, hydrate, or solvate thereof. As used herein, a "pharmaceutically acceptable salt" or "salt" refers to a salt of one or more compounds. Suitable pharmaceutically acceptable salts of compounds include acid addition salts which may, for example, be formed by mixing a solution of the compound with a solution of a pharmaceutically acceptable acid, such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like. As used herein, a "hydrate" refers to a crystal form where a stoichiometric or non-stochiometric amount of water is bound by non-covalent intermolecular forces into the crystal structure. As used herein, a "solvate" refers to a crystal form where a stoichiometric or non-stoichiometric amount of solvent, or mixture of solvents, is incorporated into the crystal structure. Examples of solvents are water, acetone, ethanol, methanol, propanol, dichloromethane, etc.

In an exemplary embodiment, the compound can be administered in a pharmaceutically acceptable carrier. The phrase "pharmaceutically acceptable carrier" as used herein means a pharmaceutically-acceptable material, composition or vehicle, such as a liquid or solid filler, diluent, excipient, solvent or encapsulating material, involved in carrying or transporting a chemical agent. Pharmaceutically acceptable carriers include pharmaceutically acceptable salts, where the term "pharmaceutically acceptable salts" includes salts of the active compounds which are prepared with relatively non-toxic acids or bases, depending on the particular substituents found on the compounds described herein. Examples of pharmaceutically acceptable carriers are solvents, diluents, dispersion media, suspension aids, surface active agents, preservatives, solid binders, stabilizers, fillers, binding agents, lubricants, coatings, antibacterial and antifungal agents, isotonic and absorption delaying agents, and the like that are physiologically compatible. Various vehicles and carriers used in formulating pharmaceutical compositions and known techniques for the preparation thereof are disclosed in Remington's Pharmaceutical Sciences (A. Osol et al. eds., 15th ed. 1975). Pharmaceutically acceptable carriers may further comprise minor amounts of auxiliary substances such as wetting or emulsifying agents, preservatives or buffers, which enhance the shelf life or effectiveness of the pharmacological agent Such carriers enable the compounds to be formulated as tablets, pills, dragees, capsules, liquids, gels, syrups, slurries, suspensions and the like, for oral ingestion by a patient to be treated. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. In one embodiment, mannitol and magnesium stearate are used as pharmaceutically acceptable carriers.

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. In one embodiment, the mode of administration is oral delivery.

Various solid oral dosage forms can be used for administering compounds including such solid forms as tablets, gelcaps, capsules, caplets, granules, lozenges and bulk powders. The compounds can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds. In one embodiment, the sphingosine1-phosphate receptor modulator is administered in a hard gelatin capsule.

Various liquid oral dosage forms can also be used for administering compounds, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds. The compounds may be injected, for example, intravenously, in the form of an isotonic sterile solution. Other preparations are also possible. Fingolimod hydrochloride is soluble in water (>10%) as well as 0.9% saline and aqueous buffers at or below pH 2.0. It is very slightly soluble or practically insoluble in aqueous buffers at or above pH 3.0. A variety of methods are known in the art to improve the solubility of the pharmacological agent in water and other aqueous solutions. For example, U.S. Pat. No. 6,008,192 to Al-Razzak et al. teaches a hydrophilic binary system comprising a hydrophilic phase and a surfactant, or mixture of surfactants, for improving the administration of lipophilic compounds such as the pharmacological agent.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., the pharmacological agent) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the method of preparation can include vacuum drying and/or spray-drying to yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The sphingosine1-phosphate receptor modulator can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. (See, e.g., *Sustained and Controlled Release Drug Delivery Systems*, J. R. Robinson, ed., Marcel Dekker, Inc., New York, 1978; U.S. Pat. No. 6,333,051 to Kabanov et al., and U.S. Pat. No. 6,387,406 to Kabanov et al.).

Supplementary active compounds can also be incorporated into the compositions. In certain embodiments, the sphingosine1-phosphate receptor modulator is coformulated with and/or coadministered with one or more additional therapeutic agents that are useful for improving the pharmacokinetics of the pharmacological agent. A variety of methods are known in the art to improve the pharmacokinetics of the pharmacological agent. In one embodiment, Riluzole™ can be administered with the sphingosine1-phosphate receptor modulator.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In one embodiment, an initial bolus dose followed by smaller maintenance doses are administered. It is especially advantageous to formulate the compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a pharmacological agent is between 0.05 and 200 mg administered daily to a subject, either with or without food. In another embodiment, 0.1-150 mg of the sphingosine1-phosphate receptor modulators is administered. In another embodiment, 5-100 mg of the sphingosine1-phosphate receptor modulators is administered. In one embodiment, 1-5 mg of the sphingosine1-phosphate receptor modulators is administered. In one embodiment, a 0.5 mg dosage form of fingolimod hydrochloride is administered.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. It is also noted that when the sphingosine1-phosphate receptor modulator is administered along with another active agent, the dosage of one or both compounds may be decreased from the single-agent dose.

Other embodiments and used will be apparent to those skilled in the art from consideration of the specification and practice disclosed herein. All U.S. Patents and other references noted herein for whatever reason are specifically incorporated by reference. The specification and examples should be considered exemplary only with the true scope and spirit indicated by the following claims.

EXAMPLES

Example 1

Fingolimod Characterization

Fingolimod is a small molecule pro-drug with a molecular weight of 343.9 g/mol. To improve water solubility, fingolimod was purchased from LC-Labs and converted to a hydrochloride salt and analyzed using LC/MS detection. LC/MS assay development elucidated the purity and molecular weight of the fingolimod. Sterility and endotoxin were generally not a significant concern since the Sphingosine1-phosphate receptor modulators were chemically synthesized. The identity and purity of fingolimod hydrochloride were tested by chromatography to verify that the substance could potentially be dosed in vivo (sterility, endotoxin level).

Example 2

Pharmacokinetics

The pharmacokinetic study provided reagent distribution and elimination parameters in order to guide future in vivo studies. Fingolimod is a compound with a relatively long plasma half-life and a high brain/plasma ratio (Meno-Tetang 2006). Because of the longer than usual half-life of fingolimod, the time points for PK harvest extended beyond the typical 9 point small molecule PK study executed at ALS Therapy Development Institute (ALSTDI, Cambridge, Mass.). Time points included 0, 0.083 hours, 0.25 hours, 0.5 hours, 0.75 hours, 1 hour, 2 hours, 4 hours, 6 hours, 8 hours, 12 hours, 24 hours, 48 hours, 72 hours, and 96 hours.

Figure 1B:
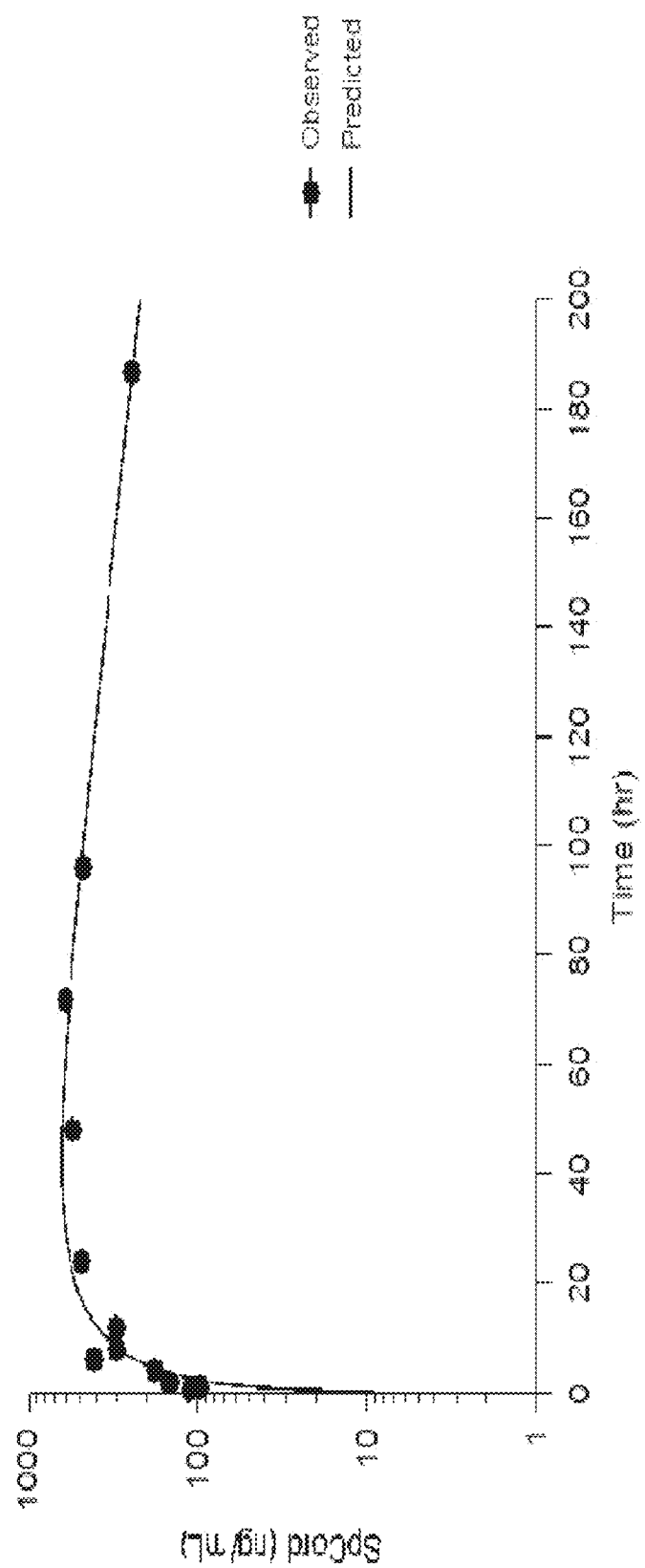
FIG. 1B is a chart showing the spinal cord pharmacokinetic profile for fingolimod in male SOD1 mice after a single IP bolus 6.7 mg/kg. The spinal cord half-life is 89.2 hours and the spinal cord $C_{max}$ is 630 ng/mL.

Fingolimod concentrations after administration of various doses to G93A-SOD1 mice was determined and is shown in FIGS. 1A and 1B. G93A-SOD1 transgenic mice (shortened to "SOD1 mice") are mutant for superoxide dismutase 1 (SOD1) and are used as a disease model because of the phenotypic and pathologic resemblance to sporadic and familial human ALS. The SOD1 mice overexpress the superoxide dismutase, CCS, to develop an accelerated disease course that is associated with enhanced mitochondrial pathology and increased mitochondrial localization of mutant SOD1. The results of the fingolimod concentration studies were consistent with published reports for fingolimod in other tissues and models. Tissues analyzed included plasma (FIG. 1A) and spinal cord (FIG. 1B). Fingolimod treated animals were then divided into two groups using two separate doping regimens:

Low Dose Fingolimod Group: IP Load 0.44 mg/kg, Maintenance 0.32 mg/kg every 7 days (q7d), and
High Dose Fingolimod Group: IP Load 2.5 mg/kg, Maintenance 1.8 mg/kg q7d.

Example 3

In Vivo Functional Activity

Figure 2A:
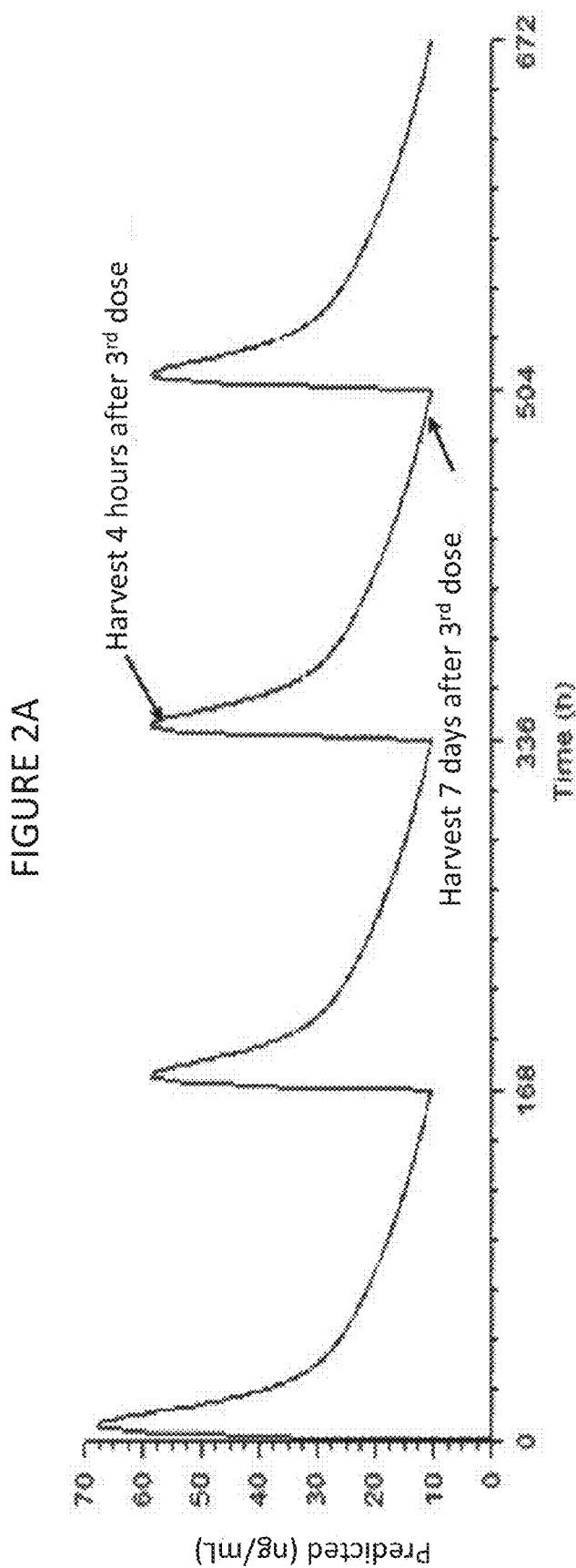
FIG. 2A is a chart showing the predicted plasma fingolimod concentration in male SOD1 mice after an initial fingolimod loading dose of 2.5 mg/kg followed by maintenance doses of 1.8 mg/kg IP given every 7 days (q7d).
Figure 2B:
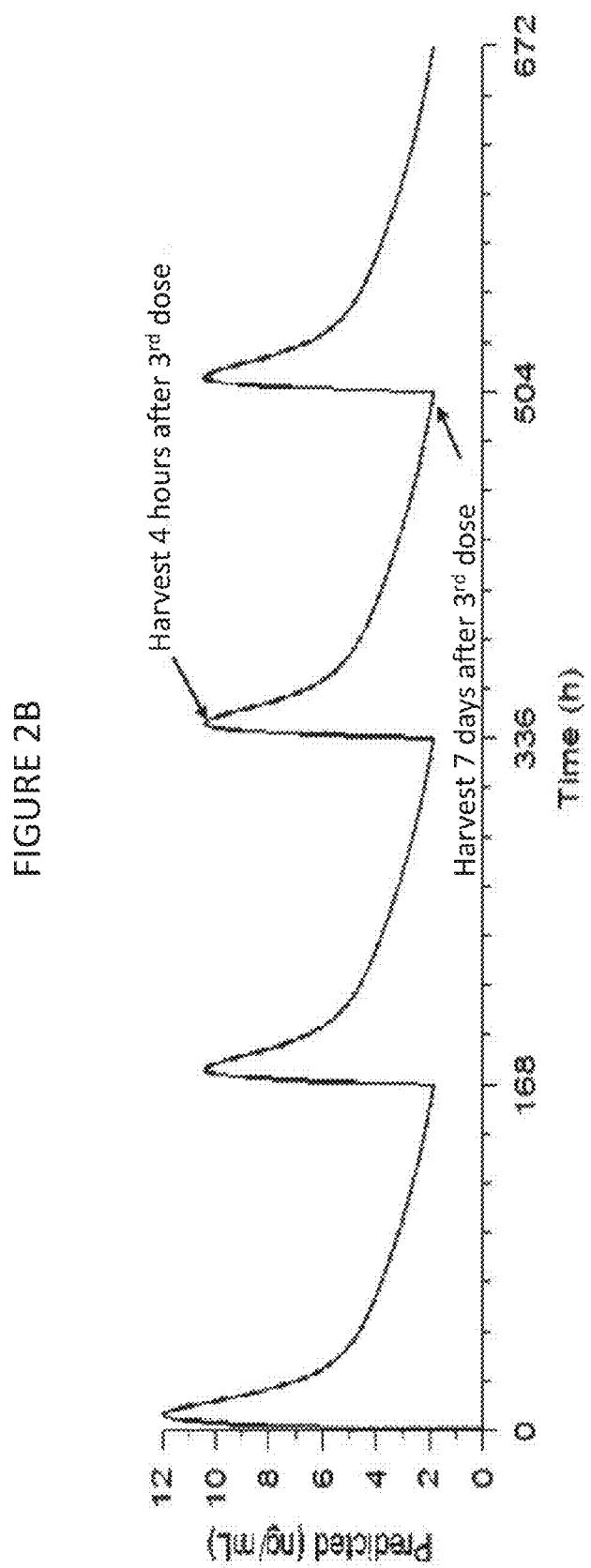
FIG. 2B is a chart showing the predicted plasma fingolimod concentration in male SOD1 mice after an initial fingolimod loading dose of 0.44 mg/kg followed by maintenance doses of 0.32 mg/kg IP given q7d.

The following dosage regimen was used to determine the dose dependent effects of fingolimod in SOD1 mice:
Cohorts:
1) SOD1 Fingolimod Treated "High Dose" (Load 2.5 mg/kg, 1.8 mg/kg Oral q7d)
   4 hour post final dose harvest
   7 day post final dose harvest
2) SOD1 Fingolimod Treated "Low Dose" (Load 0.44 mg/kg, 0.32 mg/kg Oral q7d)
   4 hour post final dose harvest
   7 day post final dose harvest
3) SOD1 Vehicle Control
   4 hour post final dose harvest
   7 day post final dose harvest The predicted plasma fingolimod load for both the high dose and the low dose regimes were determined, see FIGS. 2A and 2B. Tissues were harvested 4 hours after the third fingolimod dose. This time point was selected to best characterize the behavior of lymphocytes in animals treated with fingolimod when circulating levels of the drug are near peak concentration.

Figure 3A:
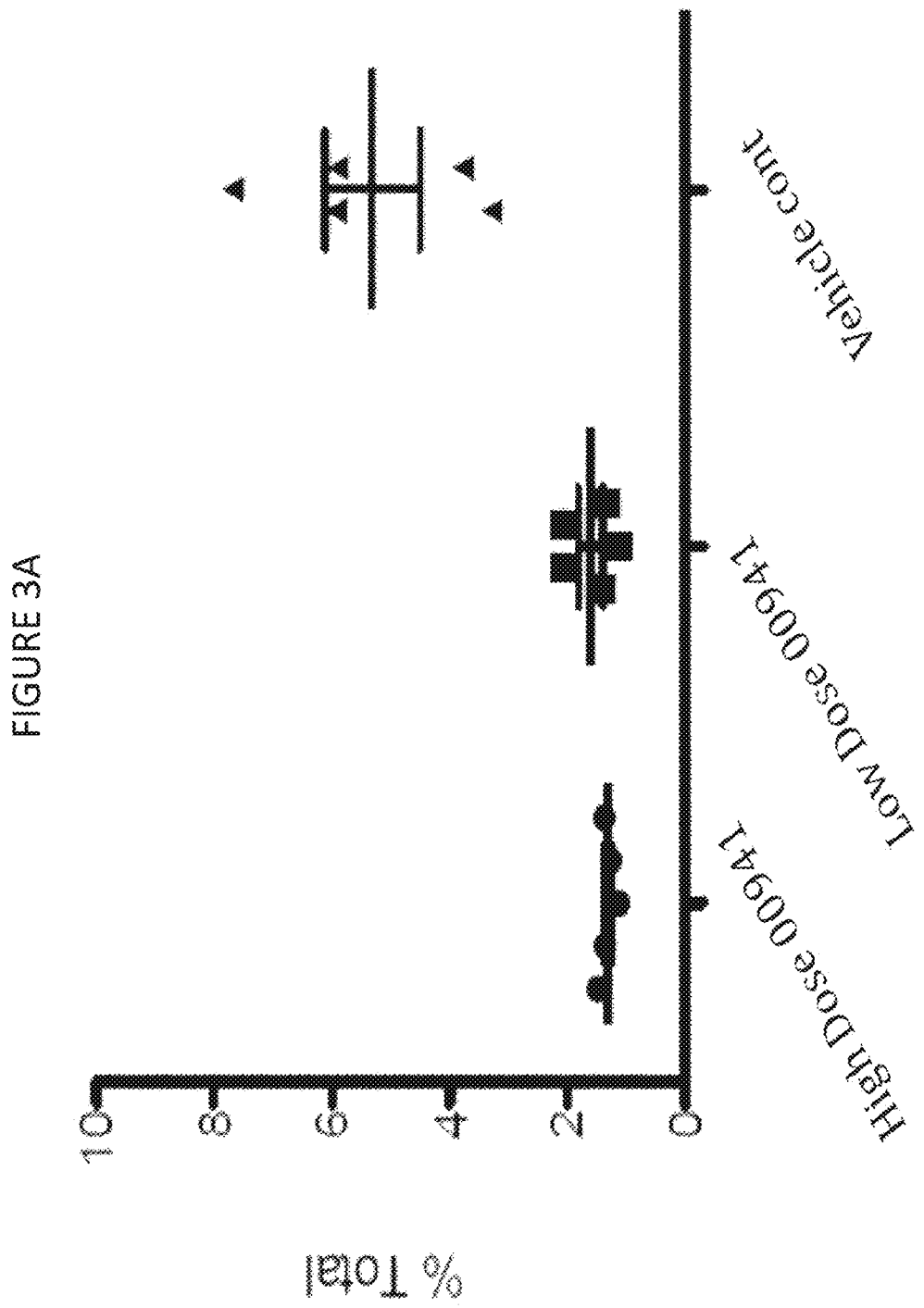
FIG. 3A is a fluorescent activated cell sorting (FACS) analysis showing the reduction of CD8+ lymphocytes in the circulation of male SOD1 mice that results from fingolimod treatment. A high dose of fingolimod (IP Loading Dose 2.5 mg/kg, Maintenance Dose 1.8 mg/kg q7d), a low dose of fingolimod (IP Loading Dose 0.44 mg/kg, Maintenance Dose 0.32 mg/kg) and a vehicle control group were tested over 14 days. Tissues were harvested 4 hours after the third dose. This time point was selected to best characterize the behavior of lymphocytes when circulating levels of the drug were near peak.
Figure 3B:
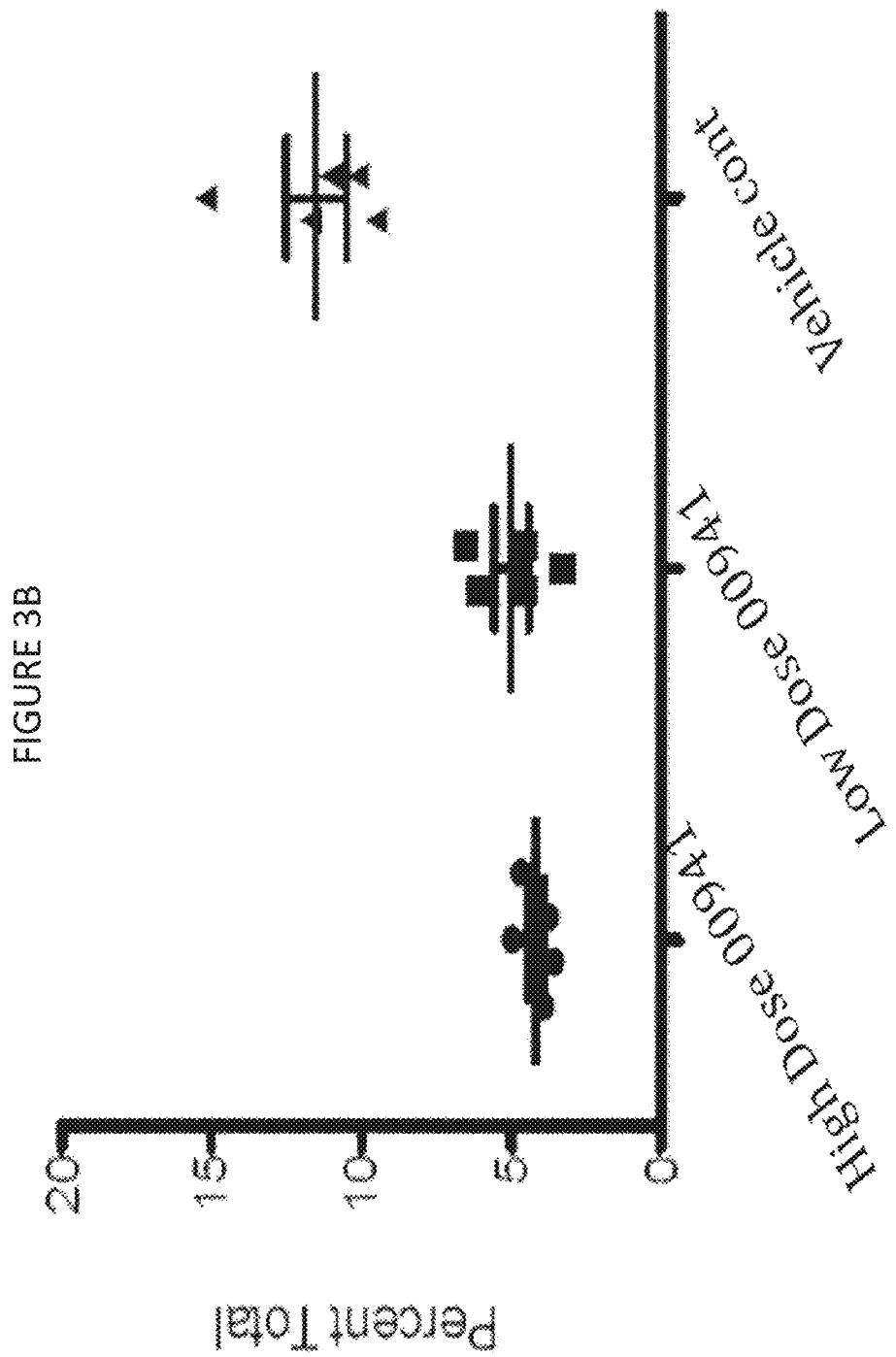
FIG. 3B is a FACS analysis showing the reduction of CD4+ lymphocytes in the circulation of male SOD1 mice that received fingolimod treatment. Dosing of fingolimod and time points were the same as in FIG. 3A.

FIGS. 3A and 3B show the level of fingolimod in whole blood after administration of a high dose of fingolimod, a low dose of fingolimod, or a vehicle control. FIG. 3A shows that the CD8+ cells in whole blood were reduced from approximately 5% in the control to less than 2% for both the high dose and low dose studies. FIG. 3B shows that the CD4+ cells in whole blood were reduced from approximately 12% in the control to approximately 5% in both the high dose and low dose studies. For both CD8+ and CD4+ cell studies, the high dose provided a greater decrease in lymphocyte concentrations compared to the low dose. A significant reduction in CD8+ cell was observed, over three-fold or 66%. The reduction in CD4+ cells was also significant, with a reduction of over two-fold or at least 50%.

Treated animals in both groups had fewer circulating CD4, CD8, and CD45R positive cells in whole blood.

Example 4

Macrophage Infiltration

Fingolimod treatment has also shown the ability to block macrophage infiltration into peripheral axons, leading to an amelioration of ALS in animal models. SOD1 animals were treated with a loading dose of 2.5 mg/kg fingolimod, followed by weekly oral dosing of 1.8 mg/kg. Dosing was initiated at 50 days of age for the three cohorts:
1) Non transgenic controls
2) untreated SOD1
3) SOD1 Fingolimod Treated "High Dose" (Load 2.5 mg/kg, 1.8 mg/kg Oral q7d)

Gastrocnemius muscle was harvested from non-transgenic control, untreated SOD1 and fingolimod treated animals at 100 days of age. Tissues were immediately embedded in OCT after harvesting. Frozen sections were H&E stained and hybridized with antibodies to detect macrophages ($\alpha$CD11b antibody).

At day 100, significant infiltration of CD11b positive macrophages was detected in tissues from untreated SOD1 animals. As expected, the macrophages appeared to be localized to the axons of nerves innervating the skeletal muscle. In contrast, animals treated with fingolimod had significantly fewer CD11b positive macrophages infiltrating the skeletal muscle. Also, no infiltrating macrophages were detected in tissues from non-transgenic control animals.

Example 5

Treatment with Fingolimod Trends Toward Prolonging Survival in hSOD1$^{G93A}$ Mice To assess the impact of reducing T lymphocyte cell proliferation on disease progression in the SOD1 preclinical animal model, fingolimod was administered to SOD1 mice and parameters of disease progression were measured, including daily measurements of neurological severity score, as well as T lymphocyte cell proliferation.

Neurological scores for both hind legs were assessed daily for each mouse from 50 days of age. The neurological score employed a scale of 0 to 4 that was developed by observation at ALSTDI (Scott et al., 2008). Briefly, animals were assigned a score of 0 if they showed full extension of their hind legs away from the lateral midline when the mouse was suspended by its tail, and the mouse could hold this position for 2 seconds, suspended 2-3 times. Animals were assigned a score of 1 when they displayed collapse or partial collapse of leg extension towards lateral midline (weakness) or trembling of hind legs during tail suspension. Animals were assigned a score of 2 when the toes curled under at least twice during walking a distance of 12 inches, or any part of the foot was dragging along the cage bottom/table. Animals were assigned a score of 3 when they had rigid paralysis or minimal joint movement, or a foot was not being used for forward motion. Animals were assigned a score of 4 when they could right themselves within 30 seconds after being laid on either side. At the point where at least one hind leg was scored as 2, food pellets were left on the cage bedding to permit easy access to food. If both hind legs were scored as 2, Nutra-Gel® (Bio-Serve #S4798) was provided as food in addition to food pellets placed on the cage bedding and a long sipper tube was placed on the water bottle.

Date and cause of death were recorded for each mouse. For humane reasons, animals were closely monitored and sacrificed as moribund prior to actual death using criteria for severe moribundity. To determine duration of survival reliably and humanely, the moribund state, defined as the inability of mice to right themselves 30 seconds after being placed on a side (a neurological score of 4) was used. The moribund mice were scored as "dead," and were euthanized using carbon dioxide asphyxiation.

Figure 4:
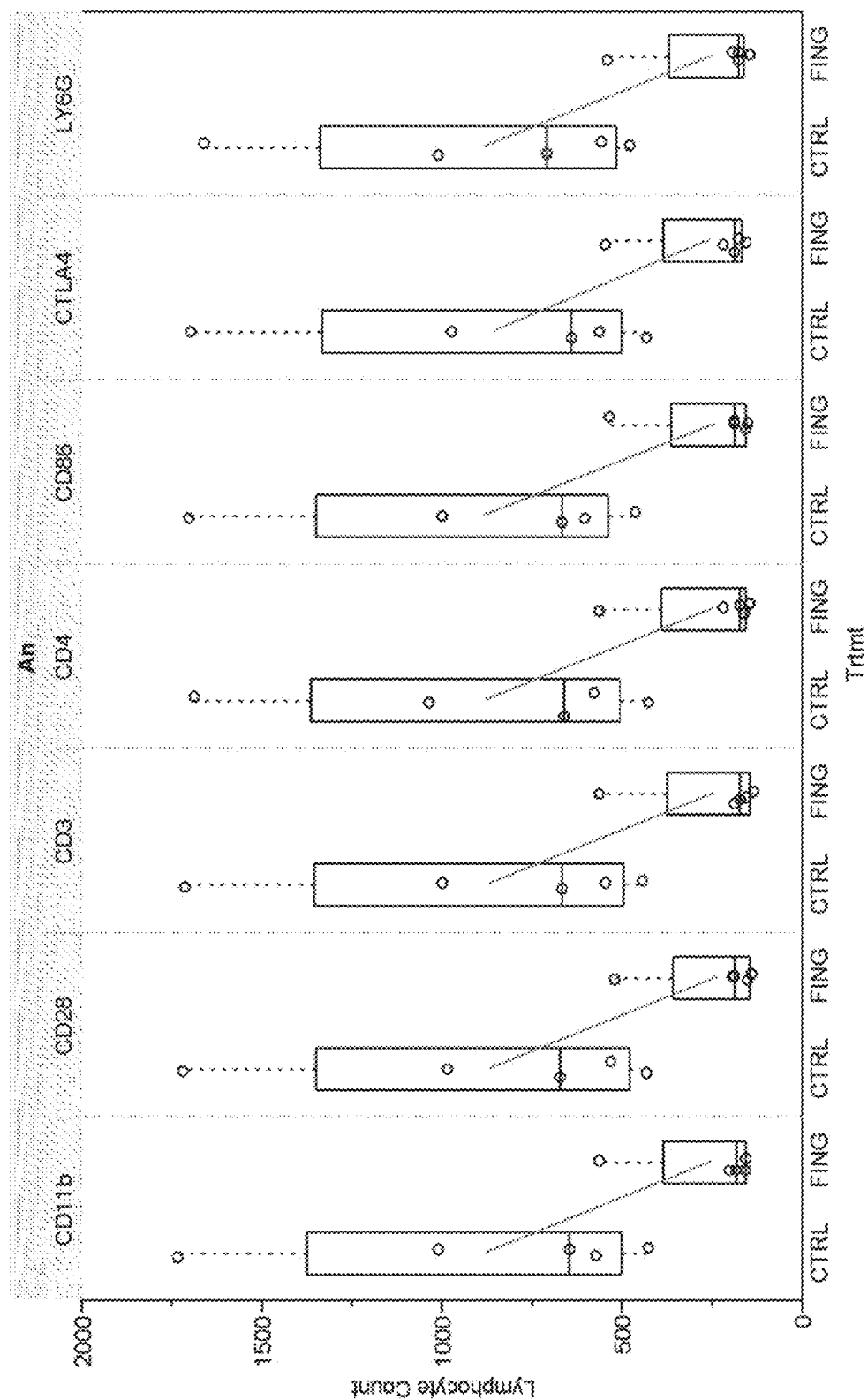
FIG. 4 is a graph showing cell counts in peritoneal lavage fluid. SOD1 animals received a loading dose of 2.5 mg/kg fingolimod orally, then oral 1.8 mg/kg once weekly for 3 weeks. Lymphocyte counts were measured via FACS for various cell surface antigens in the peritoneal lavage fluid.

SOD1 mice received a loading dose of 2.5 mg/kg fingolimod orally, then oral 1.8 mg/kg once weekly for 3 weeks. After sacrifice, several measurements were performed. To determine the lymphocyte cell count in peritoneal lavage fluid, peritoneal lavage fluid was removed after sacrifice of the animals and the peritoneal lavage fluid was subjected to fluorescent activated cell sorting for each of the cell surface antigens: CD11b, CD28, CD3, CD4, CD86, CTLA34, and LY6G. Lymphocyte cell count from SOD1 fingolimod treated mice was compared to untreated SOD1 mice in FIG. 4. For the cell surface antigens CD11b, CD28, CD4, CD86, CTLA34, and LY6G, a decreased lymphocyte count was observed in the SOD1 fingolimod treated mice.

Figure 5:
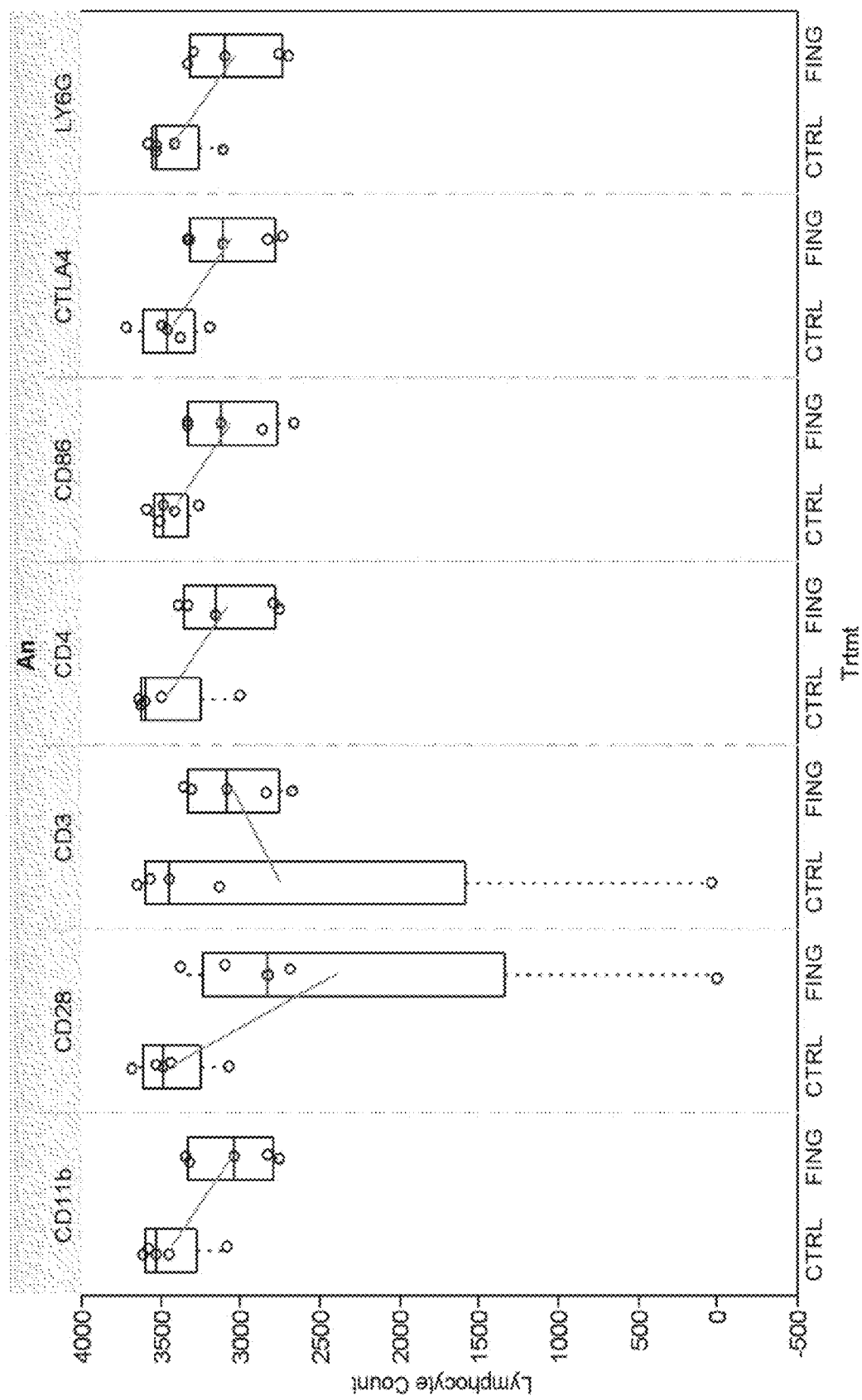
FIG. 5 is a graph showing cell counts in spleens of animals. SOD1 animals received a loading dose of 2.5 mg/kg fingolimod orally, then oral 1.8 mg/kg once weekly for 3 weeks. Lymphocyte counts were measured via FACS for various cell surface antigens in the spleen.

Lymphocytes were also measured in the spleens of SOD1 fingolimod treated mice and untreated SOD1 mice. After sacrifice, spleens were harvested from each animal and subjected to fluorescent activated cell sorting for each of the cell surface antigens: CD11b, CD28, CD3, CD4, CD86, CTLA34, and LY6G. As shown in FIG. 5, for each of these cell surface antigens, a decreased lymphocyte count in the spleen was observed for the SOD1 fingolimod treated mice compared to the untreated SOD1 mice.

Figure 6:
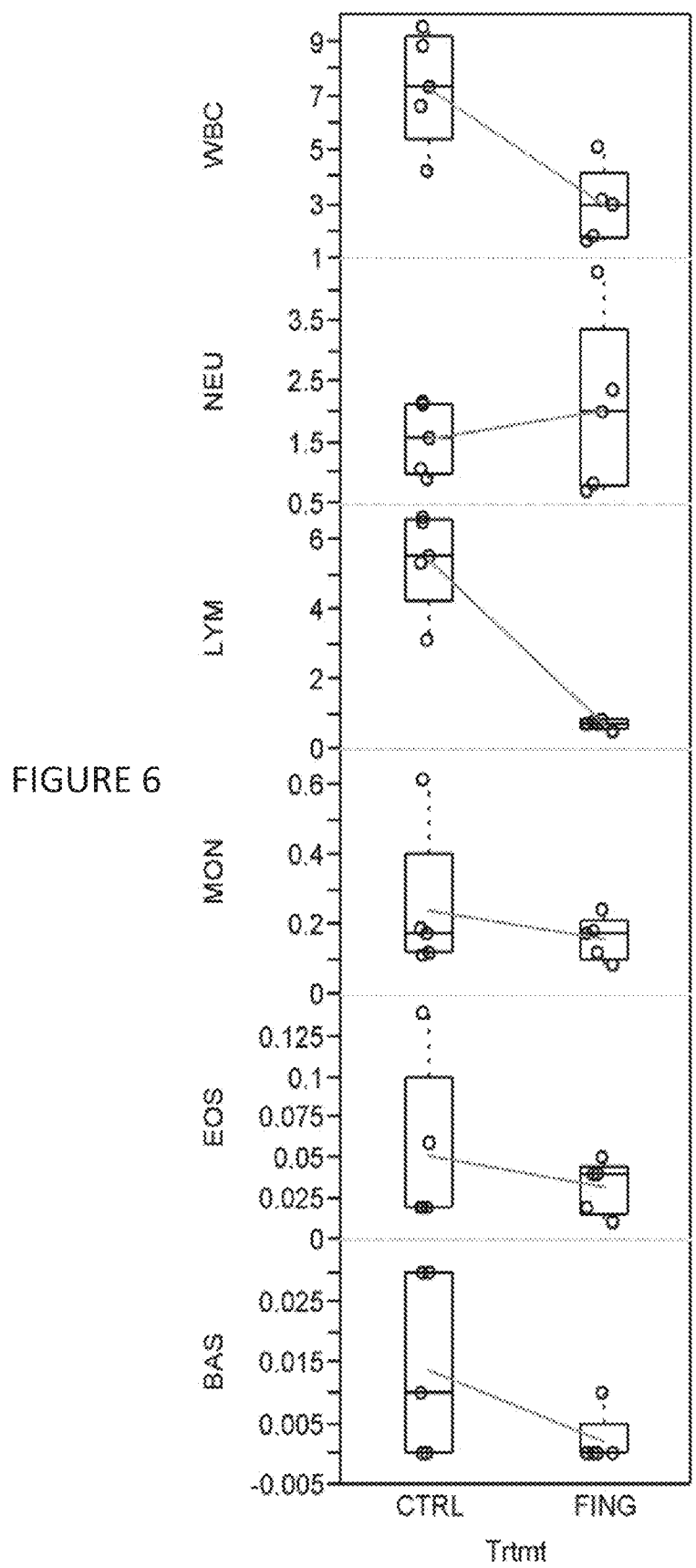
FIG. 6 is a graph showing complete blood cell counts in whole blood. SOD1 animals received a loading dose of 2.5 mg/kg fingolimod orally, then oral 1.8 mg/kg once weekly for 3 weeks. Complete blood cell counts included basophils (BAS), eosinophils (EOS), monocytes (MON), lymphocytes (LYM), neutrophils (NEU), and white blood cells (WBC).

Whole blood counts were also measured. Upon sacrifice, blood was removed and complete blood cell counts were performed. As shown in FIG. 6, a decreased cell count in blood was measured in the SOD1 fingolimod treated mice compared to the untreated SOD1 mice. In particular, basophils (BAS), eosinophils (EOS), monocytes (MON), lymphocytes (LYM), and white blood cells (WBC) all showed decreased numbers in the SOD1 fingolimod treated mice, while neutrophils (NEU) showed no significant change between the two groups.

To determine the effects of fingolimod on SOD1 mice, neurological scores were assessed. FIGS. 7A-7D show the neurological scores over time for male SOD1 mice. The black lower line represents the fingolimod-treated group (DRUG); the gray upper line represents the untreated SOD1 mice (CTRL) for each chart. An improvement in neurological score was observed in animals that received fingolimod, observed in SOD1 animals with low copy number (14-20 copies, FIGS. 7A and 7C) and high copy number (20-25 copies, FIGS. 7B and 7D) of the transgene.

Figure 8A:
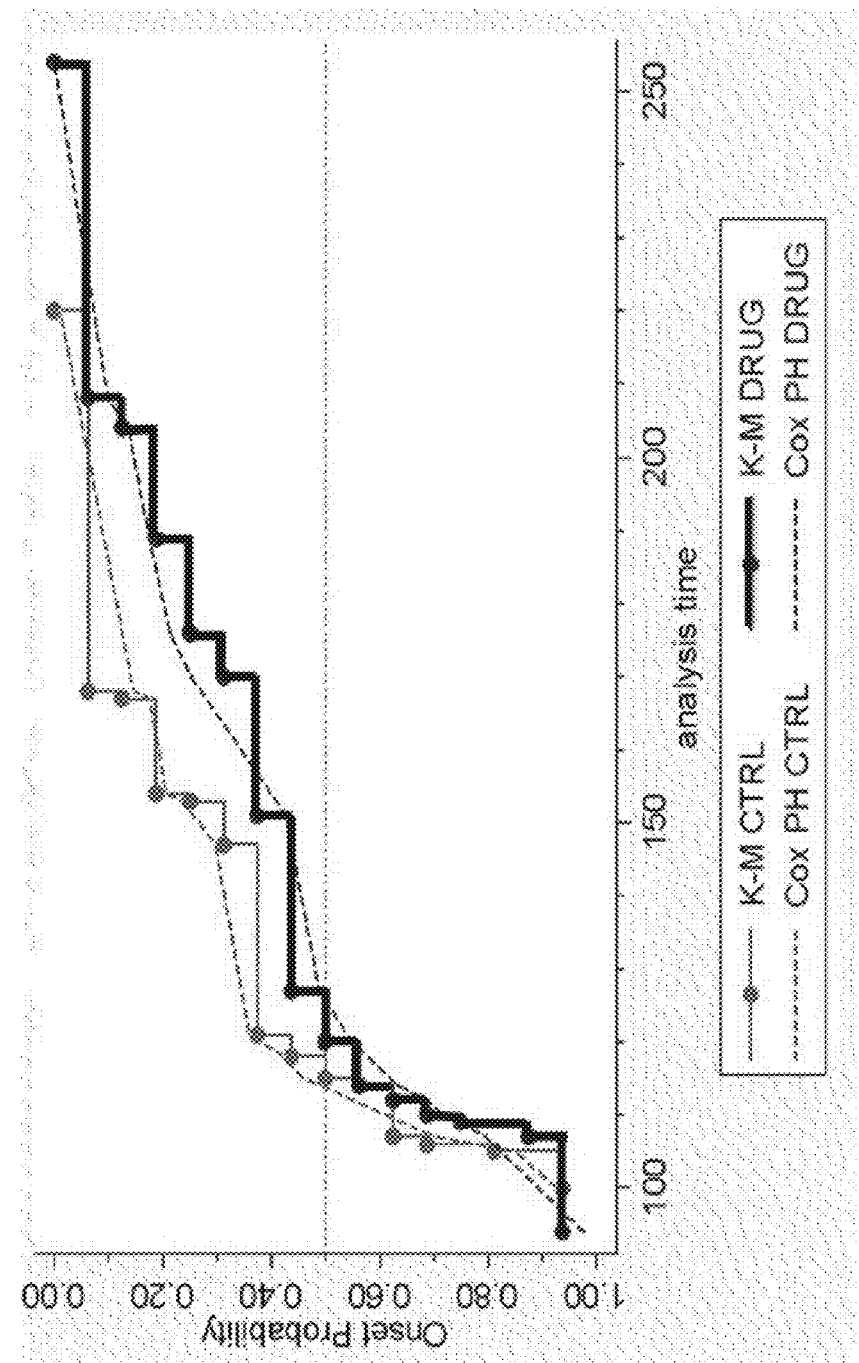
FIG. 8A is a chart comparing disease onset probability as assessed by the Cox Proportional Hazards model in untreated SOD1 and SOD1 fingolimod treated mice. The black right line represents the SOD1 fingolimod treated mice; the gray left line represents the untreated SOD1 mice.
Figure 8B:
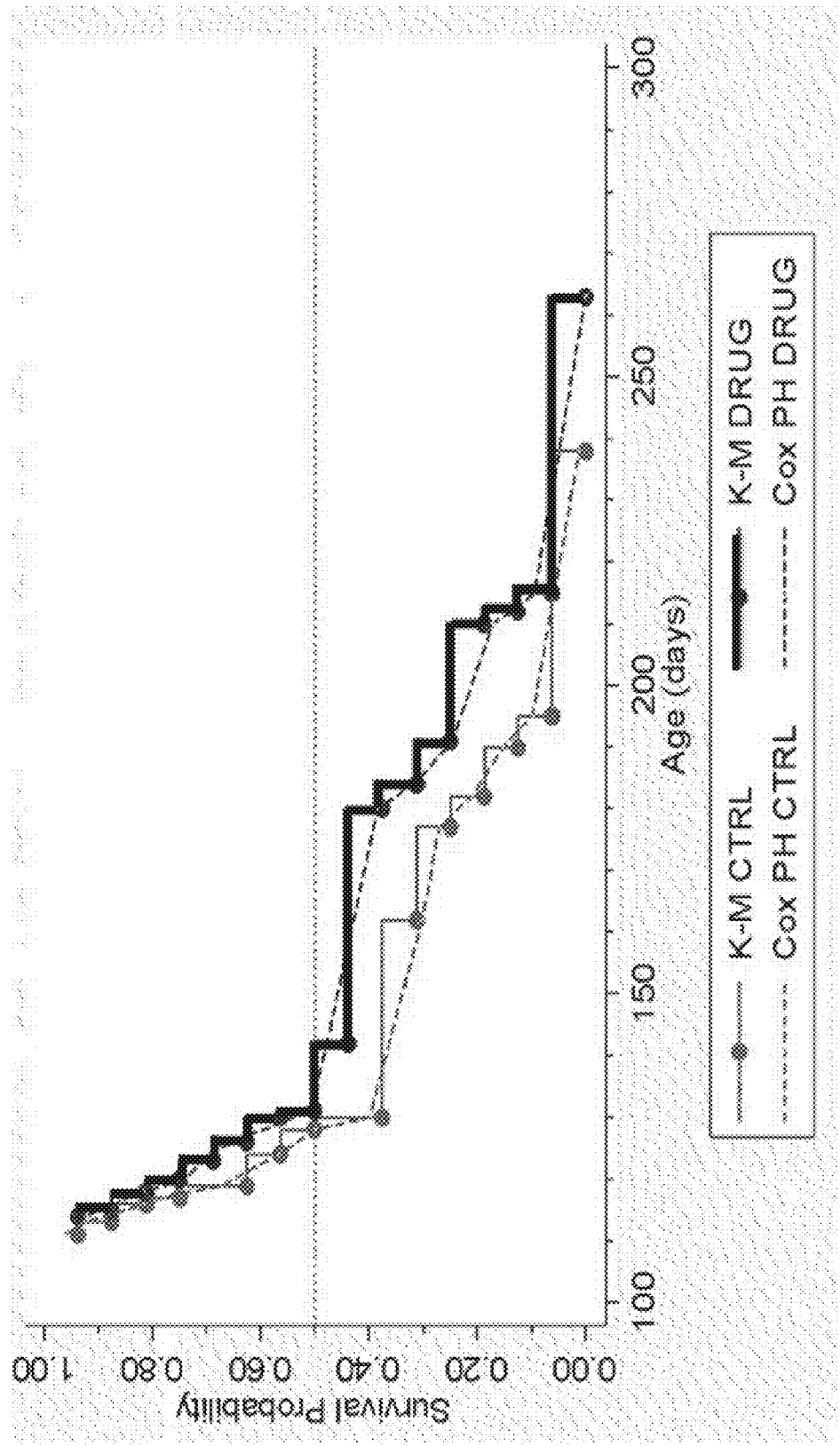
FIG. 8B is a chart comparing survival as assessed by the Cox Proportional Hazards model in untreated SOD1 mice and SOD1 fingolimod treated mice for individual animals. The black right line represents the SOD1 fingolimod treated mice; the gray left line represents the untreated SOD1 mice.

Disease onset and survival probability of the male SOD1 mice was calculated using the Cox Proportional Hazards model as shown in FIGS. 8A and 8B, respectively. In FIG. 8A, the black lower line represents the SOD1 fingolimod treated mice (DRUG) to correspond with a delayed onset of disease as compared to the untreated SOD1 mice (CTRL), gray upper line. In FIG. 8B, the black lower line represents the SOD1 fingolimod treated mice to correspond with an extended survival compared to the untreated SOD1 mice, gray upper line. FIG. 8C shows the statistical confidence of the data that demonstrates administration of fingolimod delays onset and extends survival of SOD1 mice.

Example 6

Fingolimod Treatment of hSOD1 Mice Slows Disease Progression and Improves Survival To determine the impact of reducing T lymphocyte cell proliferation on disease progression in the SOD1 preclinical animal model, a Weibull analysis was performed on the data from the animal study described in Examples 3-5.

FIG. 9A shows the reduced disease onset probability and FIG. 9B shows the increased survival probability for SOD1 fingolimod treated mice. FIG. 9C shows the difference between the Chi square values for the untreated SOD1 mice compared to the SOD1 fingolimod treated mice was 8.621 and the probability greater than Chi square was 0.0134 for the data in FIG. 9A. Likewise, FIG. 9D shows the difference between the Chi square values for the untreated SOD1 mice compared to the SOD1 fingolimod treated mice was 7.5488 and the probability greater than Chi square was 0.023 for the data in FIG. 9B. This data indicates that fingolimod was effective at reducing disease onset and increasing survival.

One skilled in the art will appreciate further features and advantages based on the above-described embodiments. Accordingly, the methods and compositions disclosed herein are not to be limited by what has been particularly shown and described, except as indicated by the appended claims. All references, patents, patent applications and other publications cited herein are expressly incorporated herein in their entirety.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A method of treating Amyotrophic Lateral Sclerosis (ALS) comprising:
    administering a compound to a subject having ALS, wherein the compound is

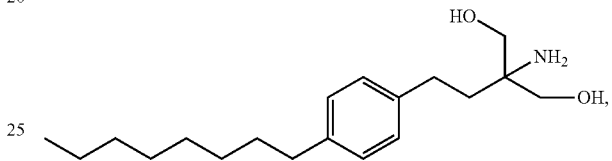

or a pharmaceutically acceptable salt, hydrate, or solvate thereof.

2. The method of claim 1, wherein the compound a hydrochloride salt, or a phosphate salt thereof.

3. The method of claim 1, wherein administering the compound to the subject having ALS inhibits macrophage accumulation.

4. The method of claim 3, wherein macrophage accumulation is localized in the axons of nerves innervating the skeletal muscle.

5. The method of claim 3, wherein inhibiting macrophage accumulation inhibits at least 50% compared to the macrophage population prior to administering the compound.

6. The method of claim 3, wherein inhibiting macrophage accumulation inhibits CD11b positive macrophages.

7. The method of claim 1, wherein administering the compound to the subject having ALS reduces lymphocyte proliferation.

8. The method of claim 7, wherein reducing lymphocyte proliferation comprises reducing the concentration of one or more of CD8+ T cell, CD4+ T cell, and CD45R+ T cell in whole blood by at least 30 percent compared to the concentration in whole blood prior to administering the compound.

9. The method of claim 7, wherein reducing lymphocyte proliferation comprises reducing the concentration of one or more of CD8+ T cell, CD4+ T cell, and CD45R+ cell in spinal fluid by at least 30 percent compared to the concentration in whole blood prior to administering the compound.

10. The method of claim 1, wherein the compound is formulated with a pharmaceutically acceptable diluent, adjuvant, or carrier.

11. The method of claim 10, wherein the compound is formulated for oral administration.

12. The method of claim 10, wherein the compound is formulated as a single daily dose.

13. The method of claim 10, wherein the compound is formulated in a dosage between 0.1 to 150 mg.

* * * * *